(12) United States Patent
Kim et al.

(10) Patent No.: US 9,765,118 B2
(45) Date of Patent: Sep. 19, 2017

(54) PHARMACEUTICAL COMPOSITION FOR CANCER PREVENTION AND TREATMENT CONTAINING PEPTIDE ORIGINATED FROM C12ORF59 PROTEIN AS AN ACTIVE INGREDIENT

(71) Applicant: KOREA RESEARCH INSTITUTE OF BIOSCIENCE AND BIOTECHNOLOGY, Daejeon (KR)

(72) Inventors: Semi Kim, Daejeon (KR); Yunhee Lee, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/664,048

(22) Filed: Mar. 20, 2015

(65) Prior Publication Data
US 2015/0259385 A1 Sep. 17, 2015

Related U.S. Application Data

(63) Continuation-in-part of application No. 13/861,879, filed on Apr. 12, 2013, now Pat. No. 9,233,139, which is a continuation-in-part of application No. PCT/KR2011/006584, filed on Sep. 6, 2011.

(30) Foreign Application Priority Data

Oct. 15, 2010 (KR) .......................... 10-2010-0100845
Sep. 5, 2011 (KR) .......................... 10-2011-0089601

(51) Int. Cl.
| A61K 38/04 | (2006.01) |
| C07K 7/64 | (2006.01) |
| C07K 7/06 | (2006.01) |
| C07K 7/08 | (2006.01) |
| A61K 47/48 | (2006.01) |
| A61K 38/17 | (2006.01) |
| A61K 38/08 | (2006.01) |
| A61K 38/10 | (2006.01) |
| A61K 38/00 | (2006.01) |

(52) U.S. Cl.
CPC ................ *C07K 7/64* (2013.01); *A61K 38/17* (2013.01); *A61K 47/48215* (2013.01); *A61K 47/48246* (2013.01); *A61K 47/48284* (2013.01); *A61K 47/48376* (2013.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS

| 8,642,737 B2 * | 2/2014 | Siekmann ........ A61K 47/48215 530/303 |
| 9,233,139 B2 * | 1/2016 | Kim ....................... A61K 38/17 |
| 2009/0163435 A1 | 6/2009 | Bader et al. |
| 2013/0202560 A1 | 8/2013 | Kim et al. |

FOREIGN PATENT DOCUMENTS

WO 2010/037859 A2 4/2010

OTHER PUBLICATIONS

Johnson et al. 84(10) British Journal of Cancer 1424-1431 (2001).*
Kamb et al. 6 Nature Reviews | Drug Discovery 115-120 (2007).*
Pearce et al. Cancer Drug Design and Discovery 424-432 (Ed. S. Neidle) (2008).*
Gura 278 Science 1041-1042 (1997).*
Extended European Search Report issued in corresponding European Patent Application No. 15160116.8 dated Jun. 8, 2015.

* cited by examiner

*Primary Examiner* — Nancy J Leith
(74) *Attorney, Agent, or Firm* — Morgan, Lewis & Bockius LLP

(57) ABSTRACT

As explained hereinbefore, the C12orf59 gene of the present invention suppresses cancer cell invasion and inhibits cancer cell survivability, and the over expression of C12orf59 protein or a fragment thereof inhibits cancer cell invasion, so that C12orf59 gene or a fragment thereof not only can be effectively used for the pharmaceutical composition for preventing and treating cancer but also can be used as a clinical marker for screening a cancer treatment agent candidate, for diagnosing various cancers or for predicting pathological stage. In addition, the C12orf59 gene or a fragment thereof of the present invention can be used for the method for preventing and treating cancer and for the preparation of a pharmaceutical composition for preventing and treating cancer.

19 Claims, 33 Drawing Sheets

Fig. 3a

```
C12orf59-1  MGVRHHVVAASALLYFILLS[....]CLTTDHVHLNYINLLVVIGALLLLCCL  60
C12orf59-2  NSWPP---------------QPCCISSCCLTTDHVHLNYINLLVVIGALLLLCCL  40

C12orf59-1  TSLCFRCCLL[........]PCEVTVIAFDHCSTLCSTITSLCSVFCPAARRILAVAH  120
C12orf59-2  TSLCFRCCLLSRCCNEECCPPPCEVTVIAFDHCSTLCSTITSLCSVFCPAARRILAVAH  100

C12orf59-1  SHSSLGCLPSSLDTLPGYEEALHMSRFTVAMCCCKAPCLPPVPEE[........]  180
C12orf59-2  SHSSLGCLPSSLDTLPGYEEALHMSRFTVAMCCCKAPCLPPVPEERCLPPTCRESTRIVD  160
```

C12orf59-1    183 (SEQ ID NO: 1)
C12orf59-2    163 (SEQ ID NO: 2)

C12orf59-1: C12orf59 isoform 1 (183 a.a.)
C12orf59-2: C12orf59 isoform 2 (163 a.a.)

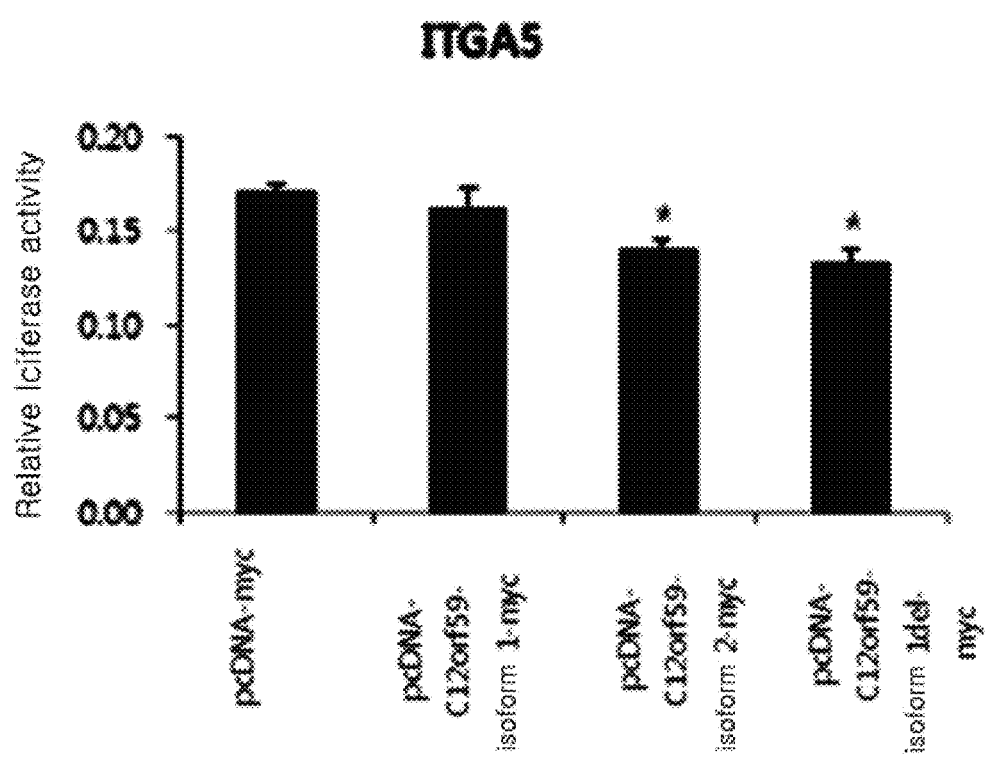

< Invasion > siGL3  sic12orf59

PHARMACEUTICAL COMPOSITION FOR CANCER PREVENTION AND TREATMENT CONTAINING PEPTIDE ORIGINATED FROM C12ORF59 PROTEIN AS AN ACTIVE INGREDIENT

SEQUENCE LISTING SUBMISSION VIA EFS WEB

A computer readable text file, entitled "SequenceListing.txt," created on or about May 28, 2015 with a file size of about 12 kb contains the sequence listing for this application and is hereby incorporated by reference in its entirety.

BACKGROUND OF THE INVENTION

1. Field of the Invention

The present invention relates to a pharmaceutical composition for preventing and treating cancer comprising C12orf59 protein or a fragment thereof, or a polynucleotide encoding the same as an active ingredient.

2. Description of the Related Art

C12orf59 (chromosome 12 open reading frame 59) gene has been well kept in human, chimpagne, dog, cow, mouse, rat, and chicken. Two isoforms of its nucleotide sequence have been reported (BC131523, 183a.a.; NM_153022, 163a.a.). This protein has been presumed as a membrane protein considering the amino acid sequence thereof, but the function of this protein has not been disclosed, yet.

In some patent descriptions (WO2010/037859 and US 2009/0163435), the involvement of C12orf59 gene in cancer has been proposed, which is though only in relation to the gene expression regulation by the treatment of anti-cancer drug. Up to date, the expression regulation and function of C12orf59 gene involved in cancer have not been explained, yet.

Cancer is one of the toughest diseases threatening human health most, which is developed by a series of cell mutation in which cells are proliferated unlimitedly and uncontrollably and hence immortalized.

A variety of biochemical mechanisms in relation to cancer have been disclosed and hence therapeutic agents have also been developed. However, any fundamental treatment method for cancer has not been established, yet. Studies have been actively undergoing to identify various biomolecules involved in cancer and thereby to develop a drug targeting such molecules, and attempts have also been made to increase cancer treatment effect by utilizing the combination of developed drugs. Therefore, it can be said that the task to identify a target molecule involved in cancer is very important.

Colorectal cancer is a kind of incurable diseases which causes million illnesses every year over the world, among which 530,000 patients are killed. This disease increases so fast as to take the third place (12.7%) of total cancer cases in Korea, which seems to be partly attributed to aging and the change in dietary pattern. The recently developed anti-cancer agents that are effective in treating colorectal cancer are exemplified by fluoropyrimidines such as 5-FU, UFT and capecitabine (product name: XELODA®); irinotecan (product name: CAMPTO®); and oxaliplatin. Seven largest pharmaceutical markets including those in USA and Europe for colorectal cancer treatment agents amount to $900 million today, which is expected to grow fast to $7,800 million in 2017. However, there are always disadvantages of continuous use of these drugs, which are resistance and side effects. Therefore, it is requested to study further to develop a novel treatment agent.

Carcinoembryonic antigen (CEA), which has been used as a marker for diagnosing colorectal cancer, is a kind of glycoproteins normally generated in the prebirth stage. The production of this protein is normally stopped before birth. If CEA level in adult is higher than that in a newborn baby, it presents the possibility of colorectal cancer or other cancers. However, the CEA level can be increased in liver cirrhosis, liver failure, and alcoholic pancreatitis patients and smokers as well. Therefore, the CEA level is used for diagnosing cancer supplementarily.

The present inventors have studied to develop a cancer diagnosis or cancer treatment agent, and as a result confirmed the expression of C12orf59 gene in cancer cell line. Particularly, when C12orf59 protein or a fragment thereof was over-expressed in cancer cell line, ITGA5 expression involved in cancer cell invasion was decreased, indicating the reduction of cancer cell invasion. When C12orf59 gene expression was suppressed in colorectal cancer cell line, cancer cell invasion was increased and cancer cell survivability was increased as well, leading to the activation of various cell signal transmission pathways. The above results indicate that C12orf59 gene has a function as a tumor suppressor. Additionally, the present invention confirmed that particular peptides originated from isoforms 1 and 2 of C12orf59 protein effectively inhibit invasion of cancer cells and metastasis. Therefore, the present inventors finally completed this invention by confirming that C12orf59 gene or protein can be effectively used for the pharmaceutical composition for preventing and treating cancer and for the method for screening cancer diagnosis or cancer treatment agent candidate substances. Additionally, the present invention was completed upon confirming that the particular peptides originated from isoforms 1 and 2 of C12orf59 proteins can be used in preventing and treating cancer.

SUMMARY OF THE INVENTION

It is an object of the present invention to provide a pharmaceutical composition for preventing and treating cancer comprising C12orf59 (chromosome 12 open reading frame 59) protein or a fragment thereof as an active ingredient.

It is another object of the present invention to provide a pharmaceutical composition for preventing and treating cancer comprising a vector containing the polynucleotide encoding C12orf59 (chromosome 12 open reading frame 59) protein or a fragment thereof or a cell containing the vector as an active ingredient.

It is also an object of the present invention to provide a pharmaceutical composition for preventing and treating cancer comprising an inducer inducing the expression or the activation of C12orf59 (chromosome open reading frame 59) protein or a fragment thereof as an active ingredient.

It is further an object of the present invention to provide a method for diagnosing or monitoring cancer by using C12orf59 (chromosome 12 open reading frame 59) gene as a marker.

It is also an object of the present invention to provide a method for screening a cancer treatment agent candidate by measuring the expression of C12orf59 gene or the activity of C12orf59 (chromosome open reading frame 59) protein or a fragment thereof.

It is also an object of the present invention to provide a method for treating cancer containing the step of administering a pharmaceutically effective dose of C12orf59 (chromosome 12 open reading frame 59) protein or a fragment thereof to a subject having cancer.

It is also an object of the present invention to provide a method for preventing cancer containing the step of administering a pharmaceutically effective dose of C12orf59 (chromosome 12 open reading frame 59) protein or a fragment thereof to a subject.

It is also an object of the present invention to provide a method for treating cancer containing the step of administering a pharmaceutically effective dose of a vector containing the polynucleotide encoding C12orf59 (chromosome 12 open reading frame 59) protein or a fragment thereof or a cell containing the vector to a subject having cancer.

It is also an object of the present invention to provide a method for preventing cancer containing the step of administering a pharmaceutically effective dose of a vector containing the polynucleotide encoding C12orf59 (chromosome 12 open reading frame 59) protein or a fragment thereof or a cell containing the said vector to a subject.

It is also an object of the present invention to provide C12orf59 (chromosome 12 open reading frame 59) protein or a fragment thereof for the preparation of an agent for preventing and treating cancer.

It is also an object of the present invention to provide a vector containing the polynucleotide encoding C12orf59 (chromosome 12 open reading frame 59) protein or a fragment thereof or a cell containing the said vector for the preparation of an agent for preventing and treating cancer.

It is also an object of the present invention to provide a method for inhibiting cancer cell invasion or metastasis, comprising administering a pharmaceutically effective dose of C12orf59 protein or a fragment thereof to a subject in need thereof.

It is also an object of the present invention to provide an isolated peptide of consisting of an amino acid sequence of the fragment of C12orf59 protein, specifically an isolated peptide consisting of an amino acid sequence selected from the group consisting of SEQ. ID. NOS: 30 to 39.

It is also an object of the present invention to provide a polynucleotide encoding the peptide.

It is also an object of the present invention to provide a vector containing the polynucleotide.

To achieve the above objects, the present invention provides a pharmaceutical composition for preventing and treating cancer comprising C12orf59 (chromosome 12 open reading frame 59) protein or a fragment thereof as an active ingredient.

The present invention also provides a pharmaceutical composition for preventing and treating cancer comprising a vector containing the polynucleotide encoding C12orf59 protein or a fragment thereof or a cell containing the said vector as an active ingredient.

The present invention also provides a pharmaceutical composition for preventing and treating cancer comprising an inducer inducing the expression or the activation of C12orf59 protein or a fragment thereof as an active ingredient.

The present invention also provides a method for detecting a protein to provide information necessary for cancer diagnosis comprising the following steps:

1) measuring the expression of C12orf59 protein or a fragment thereof in the sample originated from the subject of the experimental group;

2) comparing the expression of C12orf59 protein or a fragment thereof of step 1) with the expression of C12orf59 protein or a fragment thereof in the sample originated from the normal subject of the control group; and 3) diagnosing high risk of cancer when the expression of C12orf59 protein or a fragment thereof is lower than that of the control.

The present invention further provides a method for screening a cancer treatment agent candidate comprising the following steps:

1) treating the sample compound or composition to the cell line expressing C12orf59 protein or a fragment thereof;

2) measuring the expression of C12orf59 protein or a fragment thereof in the cell line treated in step 1); and 3) selecting the sample compound or composition as a target substance when the expression of C12orf59 protein or a fragment thereof in the cell line of step 2) is increased, compared with that of the control not treated with the sample compound or composition.

The present invention also provides a method for screening a cancer treatment agent candidate comprising the following steps:

1) treating the sample compound or composition to C12orf59 protein or a fragment thereof;

2) measuring the activity of C12orf59 protein or a fragment thereof of step 1); and 3) selecting the sample compound or composition as a target substance when the activity of C12orf59 protein or a fragment thereof of step 2) is increased, compared with that of the control not treated with the sample compound or composition.

The present invention also provides a method for treating cancer containing the step of administering a pharmaceutically effective dose of C12orf59 (chromosome 12 open reading frame 59) protein or a fragment thereof to a subject having cancer.

The present invention also provides a method for preventing cancer containing the step of administering a pharmaceutically effective dose of C12orf59 (chromosome 12 open reading frame 59) protein or a fragment thereof to a subject.

The present invention also provides a method for treating cancer containing the step of administering a pharmaceutically effective dose of a vector containing the polynucleotide encoding C12orf59 (chromosome 12 open reading frame 59) protein or a fragment thereof, or a cell containing the said vector to a subject having cancer.

The present invention also provides a method for preventing cancer containing the step of administering a pharmaceutically effective dose of a vector containing the polynucleotide encoding C12orf59 (chromosome 12 open reading frame 59) protein or a fragment thereof, or a cell containing the said vector to a subject.

The present invention also provides C12orf59 (chromosome 12 open reading frame 59) protein or a fragment thereof for the preparation of an agent for preventing and treating cancer.

The present invention provides a vector containing the polynucleotide encoding C12orf59 (chromosome 12 open reading frame 59) protein or a fragment thereof, or a cell containing the said vector for the preparation of an agent for preventing and treating cancer.

The present invention provides a method for inhibiting cancer cell invasion or metastasis, comprising administering a pharmaceutically effective dose of C12orf59 protein or a fragment thereof to a subject in need thereof.

The present invention provides an isolated peptide of consisting of an amino acid sequence of the fragment of c12orf59 protein, specifically an isolated peptide consisting of an amino acid sequence selected from the group consisting of SEQ. ID. NOS: 30 to 39.

The present invention provides a polynucleotide encoding the peptide.

The present invention provides a vector containing the polynucleotide.

Advantageous Effect

As explained hereinbefore, the C12orf59 gene of the present invention suppresses cancer cell invasion and inhibits cancer cell survivability, and the over-expression of C12orf59 protein or a fragment thereof inhibits cancer cell invasion and metastasis, so that C12orf59 gene or a fragment thereof not only can be effectively used for the pharmaceutical composition for preventing and treating cancer but also can be used as a clinical marker for screening a cancer treatment agent candidate, for diagnosing various cancers or for predicting pathological stage. In addition, the C12orf59 gene or a fragment thereof of the present invention can be used for the method for preventing and treating cancer and for the preparation of a pharmaceutical composition for preventing and treating cancer.

BRIEF DESCRIPTION OF THE DRAWINGS

The application of the preferred embodiments of the present invention is best understood with reference to the accompanying drawings, wherein:

FIG. 3a illustrates the peptide epitope sequence for the construction of Poly-C12orf59 antibody:
  The underlined third amino acid sequence indicates the peptide epitope for the construction of polyclonal antibody.

FIG. 6b illustrated the changes of promoter activity of ITGA5 after over-expressing C12orf59 protein in SW480 cell line ($*p<0.05$).

DESCRIPTION OF THE PREFERRED EMBODIMENTS

Figure 1A:
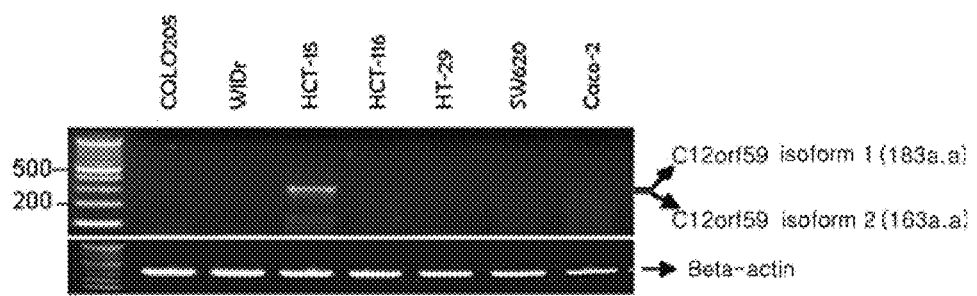
FIG. 1a illustrates the expression of C12orf59 in 7 different colorectal cancer cell lines, confirmed by semiquantitative PCR.

Hereinafter, the present invention is described in detail.

The present invention provides a pharmaceutical composition for preventing and treating cancer comprising C12orf59 (chromosome 12 open reading frame 59) protein or a fragment thereof as an active ingredient.

The said C12orf59 protein preferably has the amino acid sequence selected from the group consisting of the following amino acid sequences of 1)-3), but not always limited thereto:

1) amino acid sequence represented by SEQ. ID. NO: 1 or NO: 2;
2) amino acid sequence represented by a part of the sequence represented by SEQ. ID. NO: 1 or NO: 2; and
3) amino acid sequence demonstrating at least 80% homology with the sequence represented by SEQ. ID. NO: 1 or NO: 2.

The cancer herein is preferably selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma, but not always limited thereto.

The fragment herein preferably has the amino acid sequence selected from the group consisting of SEQ. ID. NOS: 27 to 39, but not always limited thereto. Further, the fragment comprises the amino acid sequence of SEQ. ID. NO: 38. For example, the fragment comprising the amino acid sequence of SEQ. ID. NO: 38 is selected from the group consisting of SEQ. ID. NOS: 28, 29, 30, 34 and 38, but is not limited thereto.

Also, the C12orf59 protein or the fragments thereof may have an ability to inhibit cancer cell invasion, metastasis of cancer, or both, but is not limited thereto.

The present invention also provides a pharmaceutical composition for preventing and treating cancer comprising a vector containing the polnucleotide encoding C12orf59 protein or a fragment thereof or a cell containing the said vector as an active ingredient.

The said C12orf59 (chromosome 12 open reading frame 59) protein or the fragment thereof preferably has the amino acid sequence selected from the group consisting of the following amino acid sequences of 1)-3), but not always limited thereto:

1) amino acid sequence represented by SEQ. ID. NO: 1 or NO: 2;
2) amino acid sequence represented by a part of the sequence represented by SEQ. ID. NO: 1 or NO: 2; and
3) amino acid sequence demonstrating at least 80% homology with the sequence represented by SEQ. ID. NO: 1 or NO: 2.

The said vector containing the polynucleotide encoding C12orf59 protein or a fragment thereof is preferably selected from the group consisting of linear DNA expressed in human or animal cells, plasmid vector, viral expression vector, and recombinant virus vector including recombinant retrovirus vector, recombinant adenovirus vector, recombinant adeno-associated virus (AAV) vector, recombinant herbes simplex virus vector, and recombinant lentivirus vector, but not always limited thereto, and is more preferably selected from the group consisting of pSecTag-LK68, pLXSN-LK68, rAAV-LK68, and pAAV-LK68, but not always limited thereto.

The said cell containing the polynucleotide encoding C12orf59 protein or a fragment thereof is preferably selected from the group consisting of hematopoietic stem cells, dendritic cells, NK cell and T cell, but not always limited thereto.

The cancer herein is preferably selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma, but not always limited thereto The fragment herein preferably has the amino acid sequence selected from the group consisting of SEQ. ID. NOS: 27 to 39, but not always limited thereto.

The present invention also provides a pharmaceutical composition for preventing and treating cancer comprising an inducer inducing the expression or activation of C12orf59 protein as an active ingredient.

The cancer herein is preferably selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma, but not always limited thereto.

In a preferred embodiment of the present invention, total RNA was extracted from each cell line, followed by RT-PCR to confirm the expression of C12orf59 gene in colorectal cancer, lung cancer, and stomach cancer cell lines. As a result, the expression was confirmed in colo205, HCT-15, and SW480 cell lines among the colorectal cancer cell lines (see FIG. 1a and FIG. 1b), and the expression similar to those in the said colorectal cancer cell lines was confirmed in the stomach cancer cell lines KAT0111 and NCl-N87, which was the medium level expression. It was also confirmed that the expression was comparatively high in the lung cancer cell line A549 and the stomach cancer cell lines AGS, MKN28, and MKN45, while the expression was very low in the stomach cancer cell line TMK1 (see FIG. 2).

From the above results, it was confirmed that C12orf59 gene was expressed in two different isoforms in various cancer cell lines and the expression level was different according to the cell line.

Figure 4:
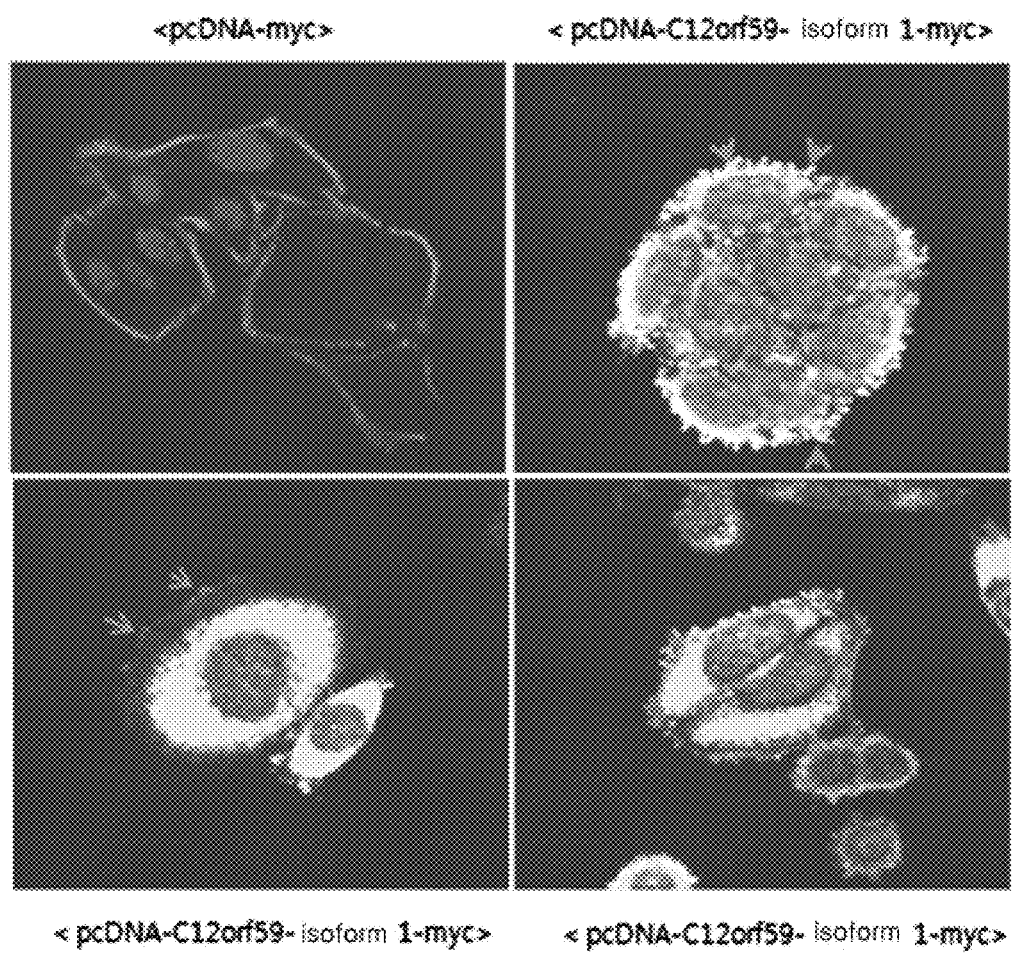
FIG. 4 illustrates the location of C12orf59 protein in the cancer cell line where C12orf59 protein was over-expressed, which was observed under confocal microscope:
  Left up: control, SW480 cell line transfected with pcDNA-myc vector;
  Left down and right: SW480 cell line transfected with pcDNA-C12orf59-isoform1-myc vector;
  White part near and inside of the cell membrane: green: C12orf59;
  Round structures in the nucleus: DAPI: nucleus;
  Border line around the cell: red: F-actin; and
  Arrow: localization example of vivid C12orf59 of the cell surface.

In another preferred embodiment of the present invention, SW480 cell line was transfected with pcDNA-C12orf59-isoform1-myc vector containing pcDNA-myc and C12orf59 construct to induce over-expression of C12orf59 therein. The intracellular location of C12orf59 protein was detected by immunofluorescence. As a result, C12orf59 was confirmed to be expressed on the surface of cancer cell (see FIG. 4).

Figure 5A:
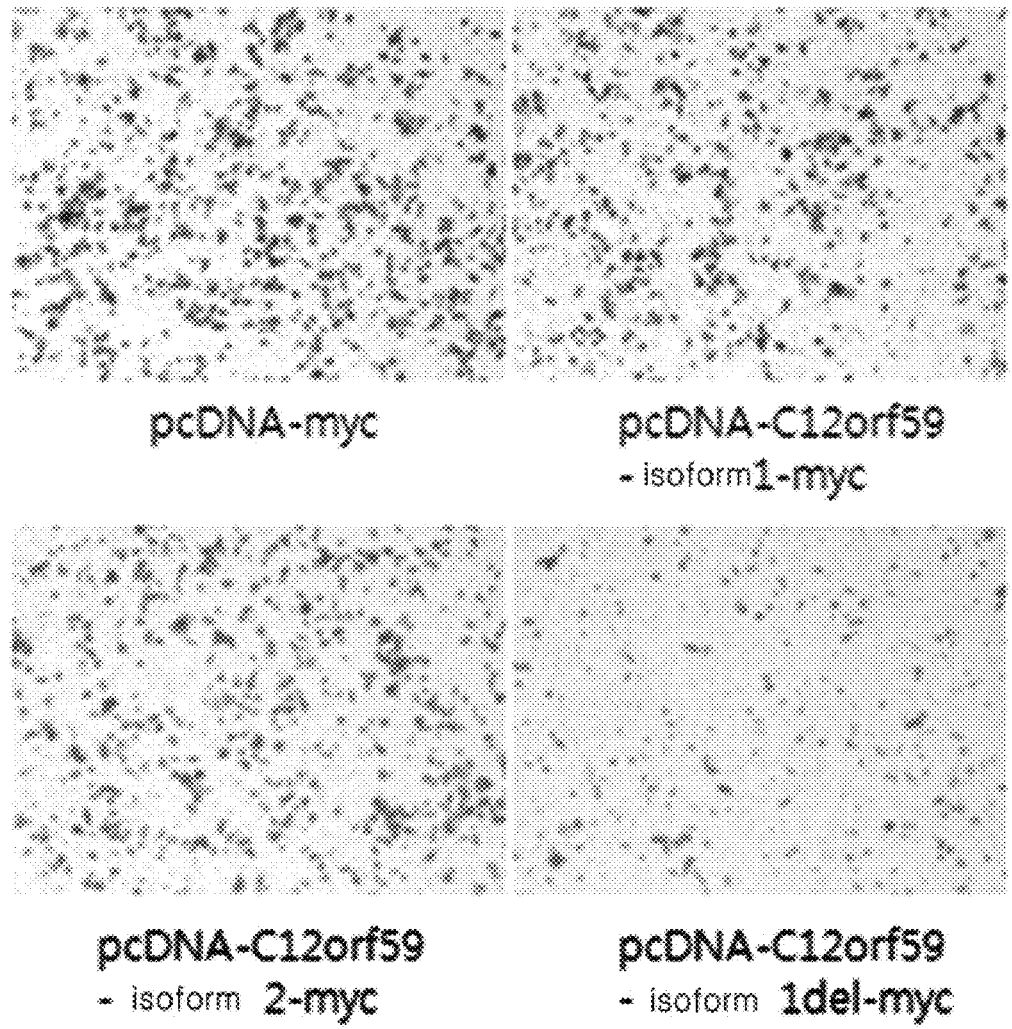
FIG. 5a illustrates the result of cancer cell invasion analysis, in which SW480 cell line was transfected with pcDNA-myc and the C12orf59 protein over-expression vectors pcDNA-C12orf59-isoform1-myc, pcDNA-C12orf59-isoform2-myc, and pcDNA-C12orf59-isoform1del-myc to over-express C12orf59 protein.
Figure 5B:
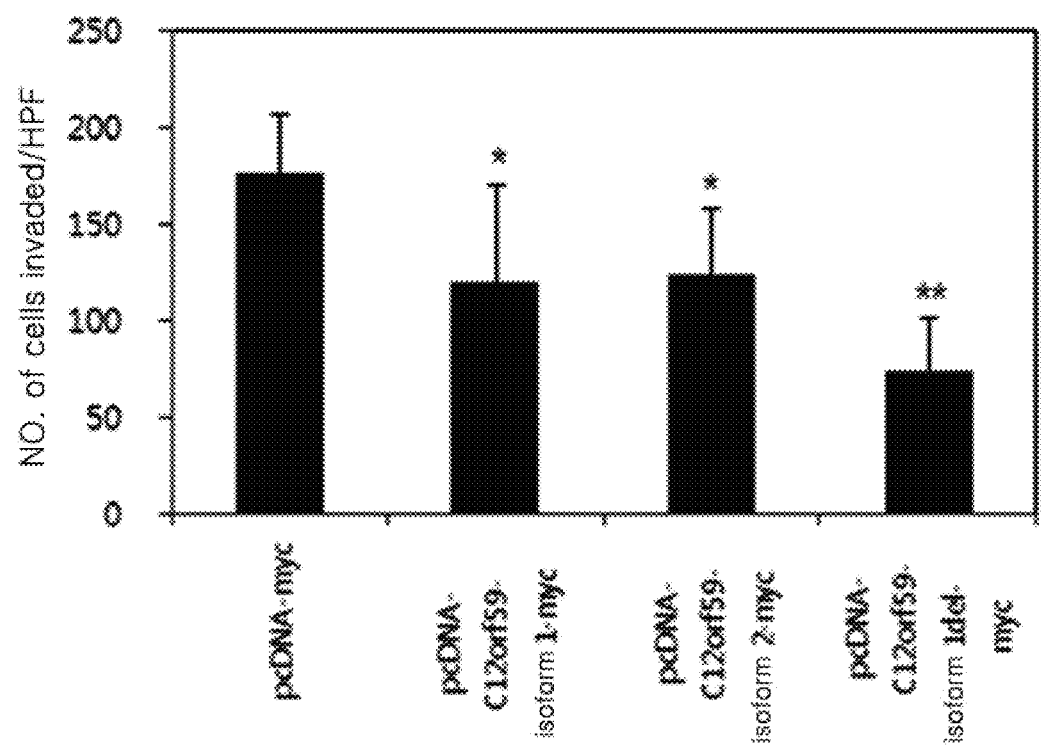
FIG. 5b illustrates the result of counting the invaded cancer cells after over-expressing C12orf59 protein in SW480 cell line ($*p<0.05$, $**p<0.001$).

In another preferred embodiment of the present invention, SW480 cell line was transfected with the vectors containing pcDNA-myc and C12orf59 construct, which were pcDNA-C12orf59-isoform1-myc, pcDNA-C12orf59-isoform2-myc, and pcDNA-C12orf59-isoform1del-myc, followed by investigation of cancer cell invasion. As a result, it was confirmed that cancer cell invasion was decreased by the over-expression of C12orf59 (see FIG. 5a and FIG. 5b). SW480 cell line was also transfected with the vectors containing pcDNA-myc and C12orf59 construct, which were pcDNA-C12orf59-isoform1-myc, pcDNA-C12orf59-isoform2-myc, and pcDNA-C12orf59-isoform1del-myc, followed by investigation of the changes of promoter activity by luciferase assay. As a result, it was confirmed that the activities of AP-1 cis element and ITGA5 promoter were decreased by the over-expression of C12orf59 (see FIG. 6a and FIG. 6b). HCT-15 cell line was transfected with the vectors containing pcDNA-myc and C12orf59 construct, which were pcDNA-C12orf-sioform1-myc, pcDNA-C12orf59-isoform2-myc, and pcDNA-C12orf59-isoform1del-myc, and with AP-1 cis-element reporter, followed by investigation of AP-1 cis-element promoter activity by luciferase assay. As a result, it was confirmed that the cis-element AP-1 activity was decreased by C12orf59 protein (see FIG. 7a). ITGA5 promoter region includes AP-1 site, and the transcription factor AP-1 induces ITGA5 expression (Corbi et al., FEBS Letters (2000) 474:201-207). Thus, the decrease of the transcription factor AP-1 activity is presumed to reduce ITGA5 expression. It is also presumed that integrin a5, a member of integrin family, which has been reported to be involved in cancer cell invasion and wound healing and to be highly expressed in those colorectal cancer cells demonstrating higher invasion ability rather than in those cells showing lower invasion ability, is playing a certain role in cancer cell migration and invasion. The present inventors then confirmed that C12orf59 protein inhibited cancer cell invasion by inhibiting the transcription factor AP-1 activity and by suppressing the expression of integrin a5 (ITGA5) in colorectal cancer cells.

In another preferred embodiment of the present invention, the colorectal cancer cell line SW480 was transfected with C12orf59 specific siRNA, followed by investigation of intracellular C12orf59 expression and cell morphology changes. As a result, it was confirmed that the expression of C12orf59 was suppressed 48 hours after the introduction of C12orf59 specific siRNA in SW480 cell line (see FIG. 8a). Morphological changes like cell diffusion and the formation of lamellipodia were also observed (see FIG. 8b).

The above results confirmed that C12orf59 siRNA could inhibit the expression of C12orf59 in cancer cell line and the inhibition of C12orf59 expression caused morphological changes of cancer cells to have high mobility form.

In another preferred embodiment of the present invention, SW480 cell line was transfected with C12orf59 specific siRNA, and then cancer cell invasion and survivability were investigated 48 hours after the transfection. As a result, it was confirmed that the inhibition of C12orf59 expression increased cancer cell invasion (see FIG. 8c) and induced anoikis (apoptosis following loss of cell anchorage)-resistance (see FIG. 10).

In another preferred embodiment of the present invention, HCT-15 cell line was transfected with C12orf59 specific siRNA, and then cancer cell invasion was investigated 48 hours after the transfection. As a result, it was confirmed that the inhibition of C12orf59 expression increased cancer cell invasion (see FIGS. 9a and 9b).

Figure 11:
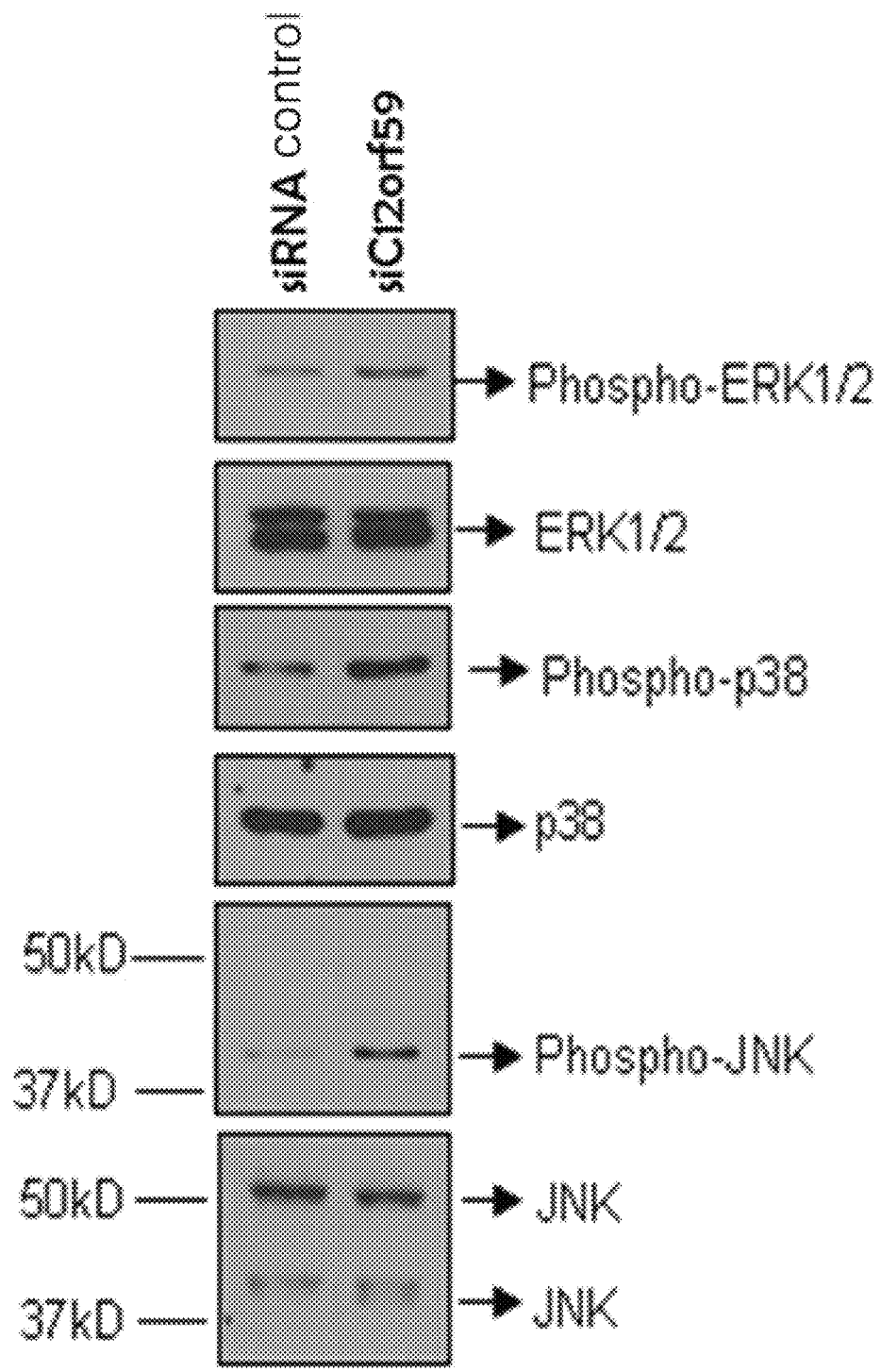
FIG. 11 illustrates the result of Western blotting confirming the changes of cell signal transmission pathways in SW480 cell line introduced with C12orf59 siRNA.

In another preferred embodiment of the present invention, the activation of cancer cell signal transmission pathway induced by C12orf59 specific siRNA was examined by Western blotting using cell lysates. As a result, it was confirmed that the phosphorylations of ERK1/2, p38, and JNK were all increased by C12orf59 specific siRNA in cancer cells (see FIG. 11), indicating that MAPK activation contributed to cancer cell invasion and survivability induced by the inhibition of C12orf59 expression. In addition, the peptide represented by SEQ. ID. NO: 28 or NO: 29 was constructed from the extracellular amino acid sequence of C12orf59 isoform 1 represented by SEQ. ID. NO: 1 or C12orf59 isoform 2 represented by SEQ. ID. NO: 2, followed by investigation of colorectal cancer cell invasion and survivability. As a result, it was confirmed that colorectal cancer cell invasion was decreased by the peptide represented by SEQ. ID. NO: 28 or NO: 29, and colorectal cancer cell survivability was also decreased thereby (see Figure and FIG. 13). From the above results, it was confirmed that the C12orf59 protein or a fragment thereof of the present invention inhibited cancer cell invasion. It was also confirmed that cancer cell invasion was increased and anoikis (apoptosis following loss of cell anchorage)-resistance was induced when the expression of C12orf59 was suppressed. Therefore, C12orf59 protein or a fragment thereof or a vector containing the polynucleotide encoding the same or a cell containing the said vector can be effectively used for the preparation of a pharmaceutical composition for preventing and treating cancer.

The pharmaceutically effective dosage of the composition of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition of the present invention can include any generally used carrier, diluent, excipient, or a combination of at least two of those. The pharmaceutically acceptable carrier can be any carrier that is able to deliver the composition of the present invention in human body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science (Mack Publishing Company, Easton Pa., 18th, 1990).

The composition of the present invention can include one or more effective ingredients having the same or similar function to C12orf59 protein or a fragment thereof. The composition of the present invention preferably includes the protein by 0.0001-10 weight %, and more preferably by 0.001-1 weight % for the total weight of the composition, but not always limited thereto.

The composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage of the composition is 0.0001~10 mg/ml per day and preferably 0.0001~5 mg/ml per day, and administration frequency is once a day or preferably a few times a day.

It is preferred to include the vector containing the polynucleotide encoding C12orf59 protein or a fragment thereof at the concentration of 0.05~500 mg and more preferably at the concentration of 0.1~300 mg. In the case of the recombinant virus containing the polynucleotide encoding C12orf59 protein or a fragment thereof, it is preferred to include at the concentration of $10^3$~$10^{12}$ IU ($10$~$10^{10}$ PFU) and more preferably at the concentration of $10^5$~$10^{10}$ IU, but not always limited thereto.

In the case that the cell containing the polynucleotide encoding C12orf59 protein or a fragment thereof is included, the composition preferably contains $10^3$~$10^8$ cells and more preferably contains $10^4$~$10^7$ cells, but not always limited thereto.

The composition of the present invention can contain a vector or a cell containing the polynucleotide encoding C12orf59 protein or a fragment thereof as an active ingredient. At this time, the effective dosage of the vector is 0.05~12.5 mg/kg, the effective dosage of the recombinant virus is $10^7$~$10^{11}$ virus particles ($10^5$~$10^9$ IU)/kg, and the effective dosage of the cell is $10^3$~$10^6$ cells/kg. Preferably, the effective dosage of the vector is 0.1~10 mg/kg, the effective dosage of the recombinant virus is $10^8$~$10^{10}$ virus particles ($10^6$~$10^8$ IU)/kg, and the effective dosage of the cell is $10^2$~$10^5$ cells/kg. The composition can be administered 2~3 times a day. The composition and the dosage thereof are not always limited to the above, and can be changed according to the patient's condition and the progress of disease.

The present invention also provides a method for detecting a protein to diagnosis cancer comprising the following steps:

1) measuring the expression of C12orf59 protein or a fragment thereof in the sample originated from the subject of the experimental group;

2) comparing the expression of C12orf59 protein or a fragment thereof of step 1) with the expression of C12orf59 protein or a fragment thereof in the sample originated from the normal subject of the control group; and 3) diagnosing high risk of cancer when the expression of C12orf59 protein or a fragment thereof is lower than that of the control.

In the method for detecting a protein to provide information necessary for cancer diagnosis, the C12orf59 expression of step 1) is preferably measured by one of the methods selected from the group consisting of Western blotting, enzyme-linked immunosorbent assay (ELISA), immunohistochemical staining, immunoprecipitation, and immunofluorescence, but not always limited thereto.

The said C12orf59 protein or the fragment thereof preferably has the amino acid sequence selected from the group consisting of the following amino acid sequences of 1)-3), but not always limited thereto:

1) amino acid sequence represented by SEQ. ID. NO: 1 or NO: 2;

2) amino acid sequence represented by a part of the sequence represented by SEQ. ID. NO: 1 or NO: 2; and 3) amino acid sequence demonstrating at least 80% homology with the sequence represented by SEQ. ID. NO: 1 or NO: 2.

The fragment herein preferably has the amino acid sequence represented by SEQ. ID. NO: 27, NO: 28 or NO: 29, but not always limited thereto.

In a preferred embodiment of the present invention, the expression of C12orf59 was confirmed in colon cancer, lung cancer, and stomach cancer cell lines. When C12orf59 was over-expressed in SW480 and HCT-15 cell lines by transfecting the cell lines with C12orf59 vecter, the expression of ITGA5 involved in cancer cell invasion was reduced, indicating the decrease of cancer cell invasion ability. When the expression of C12orf59 was suppressed by treating SW480 cell line with C12orf59 siRNA, not only cancer cell invasion and cancer cell survivability were increased but also intracellular signal transmission pathway was activated. When the expression of C12orf59 was suppressed by treating HCT-15 cell line with C12orf59 siRNA, cancer cell invasion ability was increased. In addition, the peptides represented by SEQ. ID. NO: 28 to 39 were constructed from the extracellular amino acid sequence of C12orf59 isoform 1 represented by SEQ. ID. NO: 1 or C12orf59 isoform 2 represented by SEQ. ID. NO: 2, followed by investigation of cancer cell invasion and survivability. As a result, it was confirmed that cancer cell invasion was decreased by the peptide represented by SEQ. ID. NO: 28 to 39, and cancer cell survivability was also decreased thereby.

From the above results, it was confirmed that the C12orf59 protein or a fragment thereof of the present invention inhibited cancer cell invasion, decreased cancer cell survivability under the condition of cell-anchorage loss, and had a function as a tumor suppressor. Therefore, the C12orf59 protein or a fragment thereof of the present invention can be effectively used for cancer diagnosis and for the method for detecting the protein to diagnose the risk of cancer by measuring the expression thereof.

The present invention also provides a method for screening a cancer treatment agent candidate comprising the following steps:

1) treating the sample compound or composition to the cell line expressing C12orf59 protein or a fragment thereof;
2) measuring the expression of C12orf59 protein or a fragment thereof in the cell line treated in step 1); and
3) selecting the sample compound or composition as a target substance when the expression of C12orf59 protein or a fragment thereof in the cell line of step 2) is increased, compared with that of the control not treated with the sample compound or composition.

The said C12orf59 protein or the fragment thereof preferably has the amino acid sequence selected from the group consisting of the following amino acid sequences of 1)-3), but not always limited thereto:

1) amino acid sequence represented by SEQ. ID. NO: 1 or NO: 2;
2) amino acid sequence represented by a part of the sequence represented by SEQ. ID. NO: 1 or NO: 2; and
3) amino acid sequence demonstrating at least 80% homology with the sequence represented by SEQ. ID. NO: 1 or NO: 2.

The fragment herein preferably has the amino acid sequence represented by SEQ. ID. NO: 27, NO: 28 or NO: 29, but not always limited thereto.

In a preferred embodiment of the present invention, the expression of C12orf59 was confirmed in cancer cell lines. When C12orf59 was over-expressed in SW480 and HCT-15 cell lines by transfecting the cell lines with the vecter expressing C12orf59 protein or a fragment thereof, the expression of ITGA5 involved in cancer cell invasion was reduced, indicating the decrease of cancer cell invasion ability. When the expression of C12orf59 was suppressed by treating SW480 cell line with C12orf59 siRNA, not only cancer cell invasion and cancer cell survivability were increased but also intracellular signal transmission pathway was activated. When the expression of C12orf59 was suppressed by treating HCT-15 cell line with C12orf59 siRNA, cancer cell invasion ability was increased. In addition, the peptide represented by SEQ. ID. NO: 28 or NO: 29 was constructed from the extracellular amino acid sequence of C12orf59 isoform 1 represented by SEQ. ID. NO: 1 or C12orf59 isoform 2 represented by SEQ. ID. NO: 2, followed by investigation of colorectal cancer cell invasion and survivability. As a result, it was confirmed that colorectal cancer cell invasion was decreased by the peptide represented by SEQ. ID. NO: 28 or NO: 29, and colorectal cancer cell survivability was also decreased thereby.

From the above results, it was confirmed that the C12orf59 protein or a fragment thereof of the present invention inhibited cancer cell invasion, decreased cancer cell survivability under the condition of cell-anchorage loss, and had a function as a tumor suppressor. Therefore, the C12orf59 protein or a fragment thereof of the present invention can be effectively used for screening of a cancer treatment agent candidate.

The present invention also provides a method for screening a cancer treatment agent candidate comprising the following steps:

1) treating the sample compound or composition to C12orf59 protein or a fragment thereof;
2) measuring the activity of C12orf59 protein or a fragment thereof of step 1); and
3) selecting the sample compound or composition as a target substance when the activity of C12orf59 protein or a fragment thereof of step 2) is increased, compared with that of the control not treated with the sample compound or composition.

The said C12orf59 protein or the fragment thereof preferably has the amino acid sequence selected from the group consisting of the following amino acid sequences of 1)-3), but not always limited thereto:

1) amino acid sequence represented by SEQ. ID. NO: 1 or NO: 2;
2) amino acid sequence represented by a part of the sequence represented by SEQ. ID. NO: 1 or NO: 2; and
3) amino acid sequence demonstrating at least 80% homology with the sequence represented by SEQ. ID. NO: 1 or NO: 2.

The fragment herein preferably has the amino acid sequence represented by SEQ. ID. NO: 27, NO: 28 or NO: 29, but not always limited thereto.

The present invention also provides a method for treating cancer, comprising administering a pharmaceutically effective dose of C12orf59 protein or a fragment thereof to a subject in need thereof.

The C12orf59 protein, fragment thereof, and cancer are as described above.

Specifically, the method may comprise administering a pharmaceutically effective dose of an isolated peptide having an amino acid sequence of the fragment of the C12orf59 protein. More specifically, the method may comprise administering a pharmaceutically effective dose of the isolated peptide having an amino acid sequence selected from the group consisting of SEQ ID NOS: 27 to 39, specifically SEQ ID NOS: 30 to 39, to a subject in need thereof.

In addition, the peptide, although not particularly limited thereto, may be in the form of a complex conjugated to a carrier, or may be a chemically modified one. This may be for increasing intracellular invasiveness, preventing degradation of the peptide, or increasing sustainability of physiological activity upon administration, but is not limited thereto.

The carrier, although not limited thereto, may be a non-naturally occurring carrier.

The carrier, although not limited thereto, may be in the form in which it is covalently bound to a protein or peptide according to the present invention.

In addition, when the carrier is administered in the form of a complex conjugated with a peptide according to the present invention, the carrier may be in the form of a protein, fatty acid, polyethylene glycol (PEG), etc. Examples of the protein may include immunoglobulin Fc fragment, serum protein such as albumin, keyhole limpet hemocyanin (KLH), and enzyme, but are not limited thereto. When the carrier is PEG, the PEG may be conjugated according to a known technology associated with PEG attachment in the art. Additionally, the protein may be fused to the peptide. For example, the protein may be directly connected to the protein as carrier or connected to the protein via a linker. When the linker is a peptidyl linker, it may result in a fusion protein.

The peptide of the present invention may be in the form of a modified peptide, of which N- or/and C-terminal is modified chemically or protected with organic compounds, or of which terminal is added with amino acids, for protection against proteolytic enzymes and for improvement of its stability. Particularly, if the peptide is chemically synthesized, its N- and C-terminal are electrically charged. In order to remove the charge, the N-terminal acetylation or/and C-terminal amidation may occur, but is not particularly limited thereto. Additionally, the peptide modification may include biotinylation, carboxymethylation (CAM), protecting groups such as Fmoc and lysine modification, etc.

Additionally, the peptide of the present invention may be a peptide including a modified amino acid or non-natural amino acid such as D-amino acids. Additionally, the modification of the peptide of the present invention may include cyclization and dimerization, but not limited thereto.

The carrier and the modification described above are known in the art, and one of ordinary skill in the art can easily conceive and perform.

The present invention also provides a method for inhibiting cancer cell invasion and metastasis, comprising administering a pharmaceutically effective dose of C12orf59 protein or a fragment thereof to a subject in need thereof.

The C12orf59 protein, the fragment thereof, and the peptide are the same as described above.

In detail, the method comprises administering a pharmaceutically effective dose of an isolated peptide having an amino acid sequence selected from the group consisting of SEQ. ID. NOS: 27 to 39, specifically SEQ. ID. NOS: 30 to 39, to a subject in need thereof.

The present invention also provides a method for preventing cancer containing the step of administering a pharmaceutically effective dose of C12orf59 protein or a fragment thereof to a subject.

The present invention also provides a method for treating cancer containing the step of administering a pharmaceutically effective dose of a vector containing the polynucleotide encoding C12orf59 protein or a fragment thereof, or a cell containing the vector to a subject having cancer.

The present invention also provides a method for preventing cancer containing the step of administering a pharmaceutically effective dose of a vector containing the polynucleotide encoding C12orf59 protein or a fragment thereof, or a cell containing the vector to a subject.

The cancer herein is preferably selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma, but not always limited thereto.

The composition for preventing or treating cancer of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The preferable dosage of the protein of the present invention is 0.738 μg~7.38 g for 60 kg adult male (FDA standard, USA), and more preferably 7.38 μg~0.738 g (12.3 mpk). The administration is preferably performed once every other day, but not always limited thereto and can be differed by patients.

The present invention also provides C12orf59 protein or a fragment thereof for the preparation of an agent for preventing and treating cancer.

In addition, the present invention provides a vector containing the polynucleotide encoding C12orf59 protein or a fragment thereof, or a cell containing the said vector for the preparation of an agent for preventing and treating cancer.

The cancer herein is preferably selected from the group consisting of colorectal cancer, stomach cancer, and lung cancer, but not always limited thereto In a preferred embodiment of the present invention, C12orf59 protein was over-expressed by using a vector containing the polynucleotide encoding C12orf59 protein or a fragment thereof. The over-expressed C12orf59 protein in cancer cell line inhibited the activity of transcription factor AP-1 involved in cancer cell invasion, and further inhibited the expression of integrin a5 (ITGA5), suggesting that the protein inhibited cancer cell invasion. Therefore, it was confirmed that the protein or a fragment thereof of the present invention can be effectively used for the preparation of a pharmaceutical composition for preventing and treating cancer.

Practical and presently preferred embodiments of the present invention are illustrative as shown in the following Examples, Experimental Examples and Manufacturing Examples.

The present invention provides an isolated peptide having an amino acid sequence selected from the group consisting of SEQ. ID. NOS: 27 to 39, specifically SEQ. ID. NOS: 30 to 39.

The peptide is the same as described above.

The present invention provides a polynucleotide encoding the above peptide.

The present invention provides a vector containing the polynucleotide.

However, it will be appreciated that those skilled in the art, on consideration of this disclosure, may make modifications and improvements within the spirit and scope of the present invention.

Example 1: Culture of Cancer Cell Lines

WiDr and Caco-2 cell lines were cultured in MEM (minimal essential medium: GIBCO, USA) containing 10% FBS (fetal bovine serum: GIBCO, USA), penicillin-streptomycin, L-glutamine, sodium pyruvate, and nonessential amino acids.

HCT116, HT29, Colo205, SW480, SW620, HCT15, SKOV-3, and IGROV-1 cell lines were cultured in RPMI1640 (GIBCO, USA) containing 10% FBS, penicillin-streptomycin, L-glutamine, and sodium pyruvate. HEK293E (Human Embryonic Kidney 293E) cell line was cultured in DMEM (Dulbeco's Modified Eagle Medium: GIBCO, USA) containing 10% FBS, penicillin-streptomycin, L-glutamine, sodium pyruvate, and glucose.

The lung cancer cell line A549 and the stomach cancer cell line AGS, KATOIII, MKN28, MKN45, NCI-N87, SNU-216, SNU-638, SNU-668, SNU-719, and TMK1 were cultured in RPMI1640 (GIBCO, USA) containing 10% FBS, penicillin-streptomycin, L-glutamine, and sodium pyruvate.

MKN28, MKN45, SNU-216, SNU-638, SNU-668, and SNU-719 cell lines were provided from Korean Cell Line Bank (Seoul), and TMK1 was provided from professor Park of Chonnam National University Hwasun Hospital (Chonnam, Korea). Other cell lines were provided from ATCC and all the cell lines were cultured at 37° C. with 5% $CO_2$. In addition, SW480sub cell line is a subpopulation isolated from SW480 cell line with high invasion ability.

Example 2: Confirmation of C12orf59 Gene Expression in Cancer Cell Line

To confirm the expression of C12orf59 gene in cancer cell line, total RNA was extracted by using TRIZOL® (Invitrogen) from the various cell lines cultured under the conditions described in <Example 1>. Then, RT-PCR was performed with the total RNA.

Particularly, RT-PCR was performed as described in the below diagram. The primer sequences were as follows: the forward primer: 5'-cagccctgctgtatttcatcc-3' (SEQ. ID. NO: 3), and the reverse primer: 5'-ggccaaacaccgactgcag-3' (SEQ. ID. NO: 4). cDNA was synthesized from 1 µg RNA by using cDNA synthesis pre-mix kit (cat. K-2046, Bioneer, Korea).

TABLE 1

| RT-PCR conditions C12orf59_PCR | |
|---|---|
| Template (cDNA) | 3 ul |
| Forward primer (10 pmol/ul) | 1 ul |
| Reverse primer (10 pmol/ul) | 1 ul |
| dNTP (2.5 mM) | 2 ul |
| 10x Buffer | 2 ul |
| h-taq.pol (Solgent, SHT06-R250) | 0.2 ul |
| DW | 10.8 ul |
| total | 20 ul |

In the meantime, as for the internal control of PCR, beta-actin was used. At this time, the primers used were as follows: the forward primer: 5'-GCTCGTCGTCGA-CAACGGCTC-3' (SEQ. ID. NO: 5) and the reverse primer: 5'-CAAACATGATCTGGGTCATCTTCTC-3' (SEQ. ID. NO: 6). The obtained PCR product was electrophoresed on 2% agarose gel, or 5% or 8% polyacrylamide gel to confirm the expression.

Figure 1B:
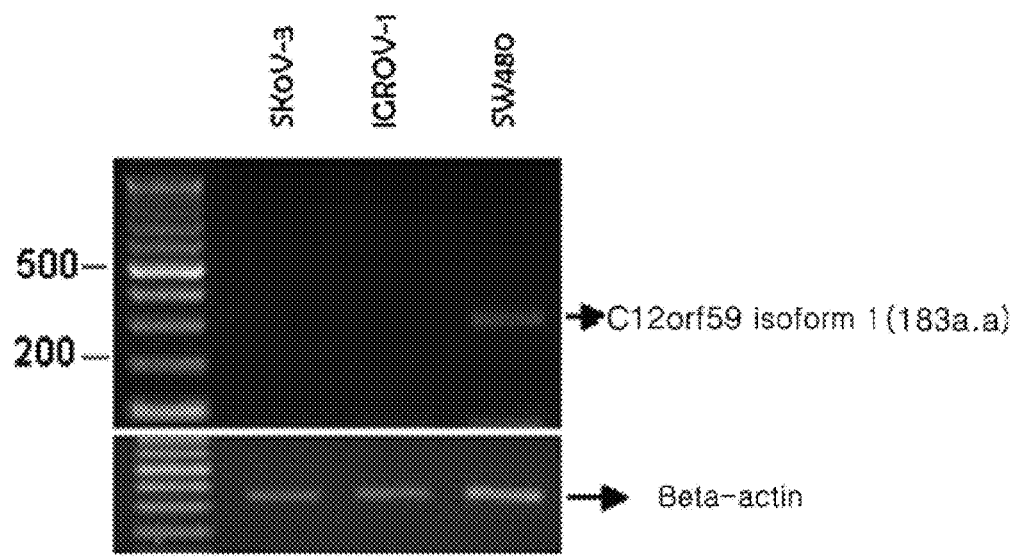
FIG. 1b illustrates the expression of C12orf59 in 2 different ovarian cancer cell lines and a colorectal cancer cell line, confirmed by semiquantitative PCR:
  SKOV-3: ovarian cancer cell line;
  IGROV-1: ovarian cancer cell line; and
  SW480: colorectal cancer cell line.

As a result, 297 bp (isoform1(183 a.a)) and 253 pb isoform2(163 a.a)) DNA fragments were amplified, according to the isoforms of C12orf59 gene. The expression was confirmed in the colon cancer cell lines Colo205 (low expression), HCT-15 (high expression), and SW480 (medium expression) (FIGS. 1a and 1b). In every cell line, 183a.a isoform was comparatively highly expressed.

Figure 2:
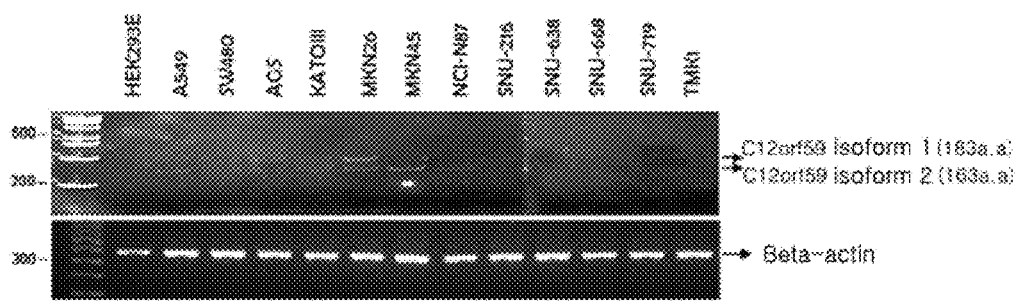
FIG. 2 illustrates the expression of C12orf59 in HEK293E, lung cancer cell line A549, stomach cancer cell line AGS, KAT0111, MKN28, NCl-N87, SNU-216, SNU-638, SNU-668, SNU-719, and TMK1, confirmed by semi-quantitative PCR.

The expression was also detected in the stomach cancer cell lines KATOIII and NCI-N87, which was also medium level expression similar to that in the colorectal cancer cell line SW480. The expression level was comparatively high in the lung cancer cell line A549, the stomach cancer cell lines AGS, MKN28, and MKN45. In the meantime, the expression level was very low in the stomach cancer cell line TMK1 (FIG. 2). The expression level of 163a.a isoform was comparatively high in the lung cancer cell line A549 and the stomach cancer cell lines MKN45 and NCl-N87.

From the above results, it was confirmed that C12orf59 gene was expressed in two different isoforms in various cancer cell lines, and the expression level was varied from each cell line.

Example 3: Construction of C12orf59 Expression Vector

Vectors in a variety forms were constructed by inserting C12orf59 gene therein in order to investigate the effect of C12orf59 expression in cancer cell lines.

Particularly, the amino acid residing next to myc in pcDNA3.1-myc his A vector (Invitrogen) sequence was selectively mutated to stop codon by using site-directed mutagenesis (QUIKCHANGE II site-directed mutagenesis kit, Stratagene). Then, PCR was performed with the vector using the primers listed in Table 2 under the condition described in Table 3. Two kinds of isoforms of C12orf59 (UniProtKB/Swiss-Prot; Q4KMG9-1 (183a.a isoform 1) and Q4KMG9-2 (163a.a isoform 2)) and 66a.a form, the amino acids ranging $1^{st}$ amino acid to $66^{th}$ of 183a.a isoform 1 where cytoplasmic domain was eliminated, were subcloned by using XhoI/HindIII. Subcloning was performed to insert stop codon right next to 183a.a isoform1, 163a.a isoform 2, and 66a.a form in order to express C12orf59 protein that was designed not to express myc protein.

TABLE 2

| | Template | | Primer Sequence | Name | SEQ ID NO |
|---|---|---|---|---|---|
| Site-directed mutagenesis | pcDNA3.1-myc-his A | A1037T & T1039A | F 5'-ctcagaagaggatctgtaaagcgccgtcgacctc-3' R 5'-gatggtcgacggcgctttacagatcctcttctgag-3' | pcDNA-myc | 13 14 |
| PCS | C12orf59-183a.a isoform1 | 183a.a isoform-myc | F 5'-accatctcgaggccgccatgggagtccgagttcat-3' R 5'-aattcaagcttgttccaagagtcaactattcg-3' | pcDNA-C12orf59-isoform1-myc | 15 16 |
| | | 66a.a form-myc | F 5'-aacatctcgaggccgccatgggagtccgagttcat-3' R 5'-aattcaagcttgcggaagcacagggac-3' | pcDNA-C12orf59-isoform1del-myc | 17 18 |
| | | 183a.a isoform-stop | F 5'-aacatctcgaggccgccatgggagtccgagttcat-3' R 5'-aattcaagctttcagttccaagagtcaactattcg-3' | pcDNA-C12orf59-isoform1 | 19 20 |
| | C12orf59-163aa isoform2 | 163a.a isoform-myc | F 5'-aacatctcgaggccgccatgtcgtggcggcctc-3' R 5'-aattcaagcttgttccaagagtcaactattcg-3' | pcDNA-C12orf59-isoform2-myc | 21 22 |
| | | 163a.a isoform-stop | F 5'-aacatctcgaggccgccatgtcgtggcggcctc-3' R 5'-aattcaagctttcagttccaagagtcaactattcg-3' | pcDNA-C12orf59-isoform2 | 23 24 |

TABLE 3

| Site-directed mutagenesis | |
|---|---|
| Template (10 ng/ul) | 2 ul |
| Primer-F (125 ng) | 1.1 ul |
| Primer-R (125 ng) | 1.1 ul |
| 10X buffer | 5 ul |
| dNTP (2.5 mM) | 2 ul |
| i-pfu (intron_25181) | 1 ul |
| DW | 37.8 ul |
| Total | 50 ul |

| PCR | |
|---|---|
| Template (10 ng/ul) | 1 ul |
| Primer-F (125 ng) | 2 ul |
| Primer-R (125 ng) | 2 ul |
| 10X buffer | 5 ul |
| dNTP (2.5 mM) | 4 ul |
| i-pfu (intron_25181) | 1 ul |
| DW | 35 ul |
| Total | 50 ul |

As a result, the recombinant vectors containing C12orf59 expression construct in pcDNA-myc his A, which were pcDNA-C12orf59-isoform1-myc, pcDNA-C12orf59- isoform1del-myc, pcDNA-C12orf59-isoform1, pcDNA-C12orf59-isoform2-myc, and pcDNA-C12orf59-isoform2, were constructed.

Example 4: Construction of Integrin α5 Promoter-Reporter

For promoter reporter assay, integrin α 5 promoter-reporter construct was prepared.

Particularly, to amplify human integrin α 5 promoter region of the colon cancer cell line SW480 genomic DNA, PCR was performed with the primers 5'-CCGCTCGAG-GAGCTGAAGGTTGGGTCC-3' (SEQ. ID. NO: 25) and 5'-CCGCTCGAGCCGTCTGTTCCCGGC-3' (SEQ. ID. NO: 26). The amplified product obtained from the PCR, integrin alpha 5 promoter region, was digested with XhoI, which was inserted in pGL3 basic vector (Promega, Southampton, UK), leading to the construction of integrin α 5 promoter-reporter construct.

Example 5: Construction of Poly-C12orf59 Antibody and Confirmation of the Effect Thereof To detect the expressed C12orf59, C12orf59 specific antibody was order-made by Young In Frontier. Particularly, polyclonal antibody was prepared by immunizing a rabbit with one of three epitopes (the $3^{rd}$ underlined amino acid sequence of FIG. 3a) highly usable for antibody construction (Young In Frontier) (FIG. 3). Western blotting was performed to confirm the prepared antibody.

Particularly, HEK293E cells were transfected with the vectors constructed in Example 3 (pcDNA-myc, pcDNA-C12orf59-isoform1-myc, pcDNA-C12orf59-isoform1, pcDNA-C12orf59-isoform2-myc, and pcDNA-C12orf59-isoform2 by using PEI reagent. 48 hours later, the cells were lysed using RIPA buffer (10 mM Tris, pH7.2, 150 mM NaCl, 1% deoxycholate, 1% Triton X-100, 0.1% SDS, 1 mM sodium orthovanadate, 50 mM NaF, 1 mM PMSF, complete protease inhibitor). The proteins in the obtained cell lysate were quantified. 30 μg of the cell lysate quantified above was mixed with SDS sample buffer, which was heated, followed by electrophoresis on 18% SDS-PAGE gel. The protein isolated by the electrophoresis was transferred onto nitrocellulose membrane, followed by blocking with 5% skim milk. The membrane was reacted with the prepared antibodies (primary antibody, 1:2000). Then, the membrane was reacted with horseradish peroxidase-conjugated secondary antibody (Bio-rad, USA). Antibody/antigen affinity was analyzed using ECL kit (ECL Plus, Amersham, USA) according to the manufacturer's instruction.

Figure 3B:
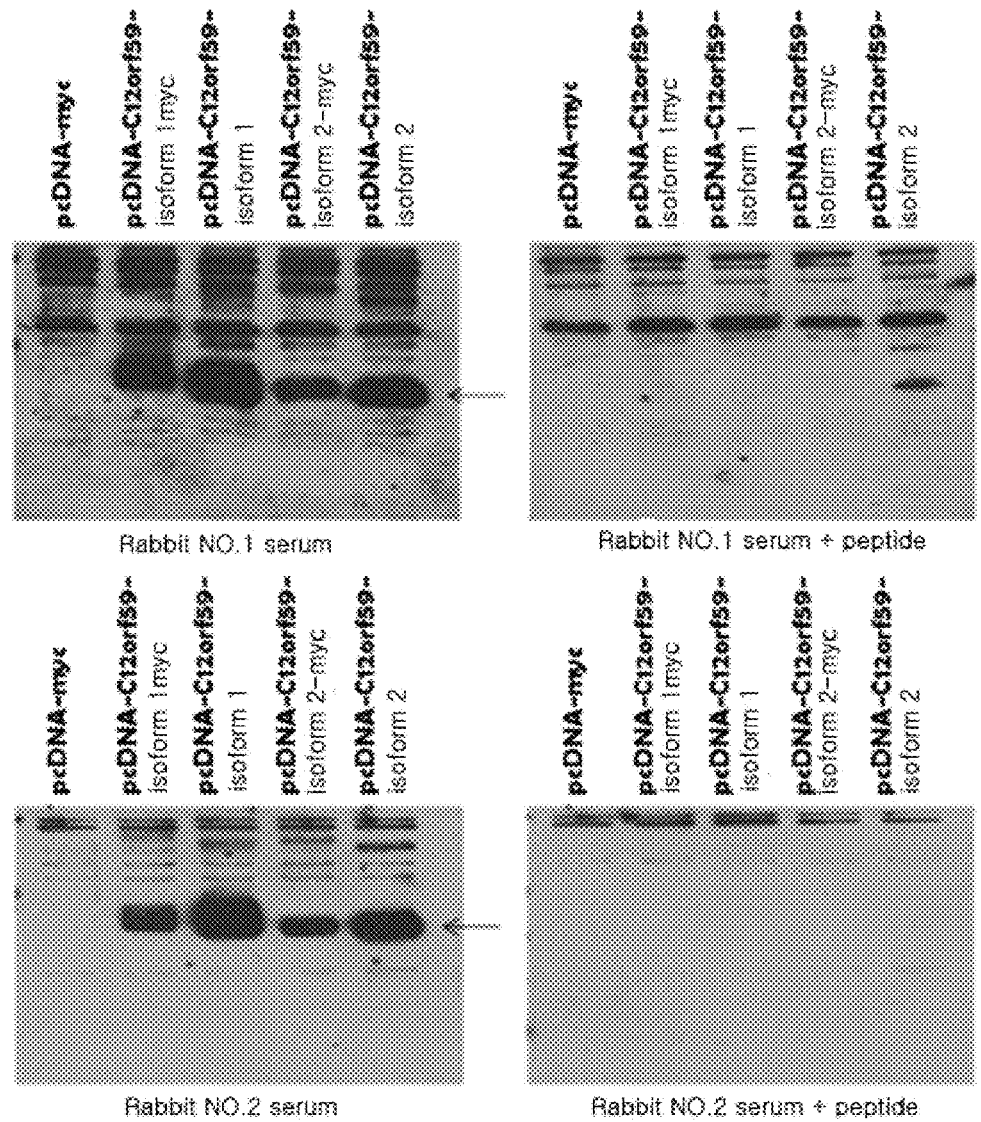
FIG. 3b illustrates the antigen specific binding capacity of the antibody constructed above:
  HEK293 cells were transfected with pcDNA-myc, pcDNA-C12orf59-isoform1-myc, pcDNA-C12orf59-isoform1, pcDNA-C12orf59-isoform2-myc, and pcDNA-C12orf59-isoform2 vectors. It was investigated by using cell lysates obtained from the above transformed cells whether or not the antibody could recognize C12orf59 protein;
  Arrow: C12orf59 protein; and
  Peptide: antigen specific binding capacity confirmed by using the antigen peptide as a blocking reagent.

As a result, it was confirmed that the two kinds of antibodies (Rabbit #1 and Rabbit #2) obtained from two rabbits did recognize clearly C12orf59 protein in the cell lysate expressing the protein (FIG. 3b, left panel, arrow). The confirmed band disappeared after the blocking using the antigen peptide blocking reagent used for the construction of antibody (FIG. 3b, right panel), indicating that the band was C12orf59 protein-specific. Therefore, it was confirmed that the order-made antibody was C12orf59 antibody specifically recognizing C12orf59 protein.

Example 6: Preparation of the Peptides Originated from C12orf59 Protein

Peptides were designed from the amino acid sequences of the extracellular domains of C12orf59 isoform1 represented by SEQ. ID. NO: 1 and isoform2 represented by SEQ. ID. NO: 2, which were order-made by Peptron Inc (Daejeon, Korea). Each peptide sequence was identified as follows:

TABLE 4

| Name | Amino acid sequence (N-term to C-term) | Number of Amino acids | SEQ ID NO |
|---|---|---|---|
| A_intact | EENCGNPEHCLTTDWVH | 17 | 28 |
| B_intact | SWRPQPCCISSCCLTTDWVH | 20 | 29 |
| A_N-term | NPEHCLTTDWVH | 12 | 30 |
| A_C-term1 | EENCGNPEHCLT | 12 | 31 |
| A_Cen | NPEHCLT | 7 | 32 |
| A_C-term2 | EENCGNP | 7 | 33 |
| B_N-term | PCCISSCCLTTDWVH | 15 | 34 |
| B_C-term1 | SWRPQPCCISSCCLT | 15 | 35 |
| B_Cen | PCCISSCCLT | 10 | 36 |
| B_C-term2 | SWRPQPCCIS | 10 | 37 |
| A/B common | CLTTDWVH | 8 | 38 |
| B_Cen2 | PCCISS | 6 | 39 |

In particular, A_intact, A_N-term, A_C-term1, A_Cen, and A_C-term2 peptides are fragments of C12orf59 isoform 1 having 183 amino acids, and A_N-term, A_C-term1, A_Cen, and A_C-term2 are parts of A_intact and consist of seven or twelve amino acids. More particularly, A_N-term is A_intact where five N-terminal amino acids were deleted, whereas A_C-term1 and A_C-term2 are A_intact where five and ten C-terminal amino acids were deleted, respectively. A_Cen is a peptide consisting of seven central amino acids of A_intact. Also, B_intact, B_N-term, B_C-term1, B_Cen, B_Cen2 and B_C-term2 peptides are a fragment of C12orf59 isoform 2 having 163 amino acids. B_N-term, B_C-term1, B_Cen, B_Cen2, and B_C-term2 are parts of B_intact and consist of fifteen, ten, or six amino acids. B_N-term is B_intact where five N-terminal amino acids were deleted, B_C-term1 and B_C-term2 are B_intact where five and ten C-terminal amino acids deleted, respectively, and B_Cen is a peptide consisting of ten central amino acids of B_intact. In addition, B_Cen2 is a peptide consisting of six central amino acids of B_intact. Also, A/B Common is a peptide consisting of eight C-terminal amino acids which are commonly present in A_intact and B_intact.

Example 7: Generation of A_Intact-Fc Fusion Protein

For in vivo efficacy evaluation, A_intact peptide fused with human Fc domain was generated. In brief, a fragment containing the coding sequence of A_intact peptide was transferred to pCMV-Fc-myc vector (Jung et al., Oncogene (2008) 27:2635-2647), which produced pCMV-A_intact-Fc-myc construct. HEK293E cells were transfected with this construct using LIPOFECTAMINE 2000. At 2 days after transfection, the medium was changed to serum-free medium. Conditioned media were obtained 5 times at 2-day intervals. Then, the secreted A_intact-Fc fusion protein was purified using protein A excellose beads (Bioprogen, Daejon, Korea) and a total of 4.5 mg was obtained.

Example 8: Synthesis of A_Intact Peptide with Terminal Modification

A_intact peptide with N-terminal acetylation and C-terminal amidation was synthesized in Peptron (Daejon, Korea).

Experimental Example 1: Effect of C12orf59 Over-Expression in Cancer Cell Line

<1-1> Confirmation of C12orf59 Location in Cancer Cell Line

To confirm the location of C12orf59 in cancer cell line, the colorectal cancer cell line SW480 was transfected with pcDNA-myc and pcDNA-C12orf59-isoform1-myc by microporation (NEON Transfection System, Invitrogen).

Particularly, SW480 cells were recovered, followed by washing with PBS. The cells were resuspended in R buffer (NEON Transfection System, Invitrogen) at the density of $3 \times 10^5$ cell/10 μl, to which pcDNA-myc and pcDNA-C12orf59-isoform1-myc vector DNAs, leading to the transfection using microporation (NEON Transfection System, Invitrogen). The cells were attached on cover slips. 48 hours later, the attached cells were fixed with 3.7% paraformaldehyde diluted in PBS, followed by washing three times with PBS. The cells were reacted with 0.3% Triton-X-100, followed by washing three times. The cells were blocked with 10% normal Goat serum, followed by reaction with C12orf59 antibody (1:500, Young In Frontier). Then, the cells were reacted with fluorescein-labeled secondary antibody (Vector lab, USA). F-actin and nucleus were stained, followed by observation under conforcal microscope.

As a result, C12orf59 protein was confirmed to exist on the cell surface (FIG. 4), which was attributed to transmembrane domain in the amino acid sequence of C12orf59.

<1-2> Changes of Cancer Cell Invasion Ability by C12orf59 Over-Expression

To investigate the changes of cancer cell invasion ability induced by C12orf59 over-expression in cancer cell lines, the colon cancer cell line SW480 was transected with pcDNA-myc, pcDNA-C12orf59-isoform1-myc, pcDNA-C12orf59-isoform2-myc, and pcDNA-C12orf59-isoform1del-myc, followed by invasion assay 48 hours later.

Particularly, the porous membrane of 24-well transwell plate (8 μm pore size; Costar, USA) was coated with 100 μl of MATRIGEL (BD Biosciences, USA) diluted in serum free medium at the concentration of 200 μg/ml for invasion assay, which stood at room temperature for 1 hour for fixing. The lower chamber of the transwell plate was coated with 100 μl of collagen type I (Sigma) at the concentration of 20 μg/ml for migration and invasion assay. The transformed cells transfected with pcDNA-myc, pcDNA-C12orf59-isoform1-myc, pcDNA-C12orf59-isoform2-myc, and pcDNA-C12orf59-isoform1del-myc by microporation as described in Experimental Example <1-1> were distributed in the upper chamber of the said 24-well transwell plate at the density of $2.5 \times 10^4$ and $3 \times 10^4$ cells respectively. Culture was performed at 37° C. with 5% $CO_2$ for 48 hours to let the cells migrate from the upper chamber to the lower chamber. The non-migrated cells were eliminated from the surface of the upper chamber. The cells migrated to the lower chamber were fixed with 3.7% paraformaldehyde dissolved in PBS, followed by staining with 2% crystal violet solution. The excessive crystal violet solution was washed off with distilled water. The selected area (×100) was photographed. The number of the cells migrated and invaded was counted from 5 different selected areas. The experiment was duplicated with the same condition to make sure the results. Data reflected migrated cells±standard error at ×200 HPF (high power field).

As a result, the transformed cells prepared by introducing pcDNA-myc, pcDNA-C12orf59-isoform1-myc, pcDNA-C12orf59-isoform2-myc, and pcDNA-C12orf59-isoform1del-myc into SW480 cell line demonstrated reduced cancer cell invasion ability when C12orf59 protein or a fragment thereof was expressed therein, except the control cell line transfected with pcDNA-myc vector (FIGS. 5a and 5b), indicating that C12orf59 could efficiently inhibit cancer cell invasion.

<1-3> Inhibition of Integrin Expression by C12orf59 Over-Expression in Cancer Cell Line It is well-known that the promoter region of integrin alpha 5 (ITGA5) includes AP-1 site and the transcription factor AP-1 induces ITGA5 expression. Therefore, decrease of the AP-1 activity can reduce the expression of ITGA5. ITGA5 has been known to be involved in cancer cell invasion and wound healing, and is up-regulated in colorectal cancer cells having high invasion ability, compared with them having low invasion ability. It has been reported that ITGA5 contributes to migration and invasion of cancer cells. Therefore, the present inventors investigated whether the decrease of cancer cell invasion by C12orf59 over-expression was attributed to ITGA5 known to be involved in cancer cell migration and invasion.

To do so, the C12orf59 over-expression vector, the reporter vector (Integrin α 5 promoter-reporter, ITGA5 promoter-reporter), and the AP-1 cis element vector (AP-1 cis-Reporting system, Stratagene) were expressed in the colorectal cancer cell line SW480. Then, the activity of each promoter therein was investigated by luciferase assay.

Particularly, $2.5 \times 10^5$ SW480 cells were distributed in 6-well plate, followed by transfection with 1.8 μg of pcDNA-myc, pcDNA-C12orf59-isoform1-myc, pcDNA-C12orf59-isoform2-myc, and pcDNA-C12orf59-isoform1del-myc along with 2 μg of reporter plasmid DNA prepared in Example 4 by using LIPOFECTAMINE 2000 reagent (invitrogen). 48 hours after the transfection, luciferase activity was measured by DUAL-LUCIFERASE reporter assay system (Promega). Transfection efficiency was measured by using Renilla luciferase activity value measured after co-transfection with 0.2 μg of Renila luciferase vector and pRL-TK (Promega).

Figure 6A:
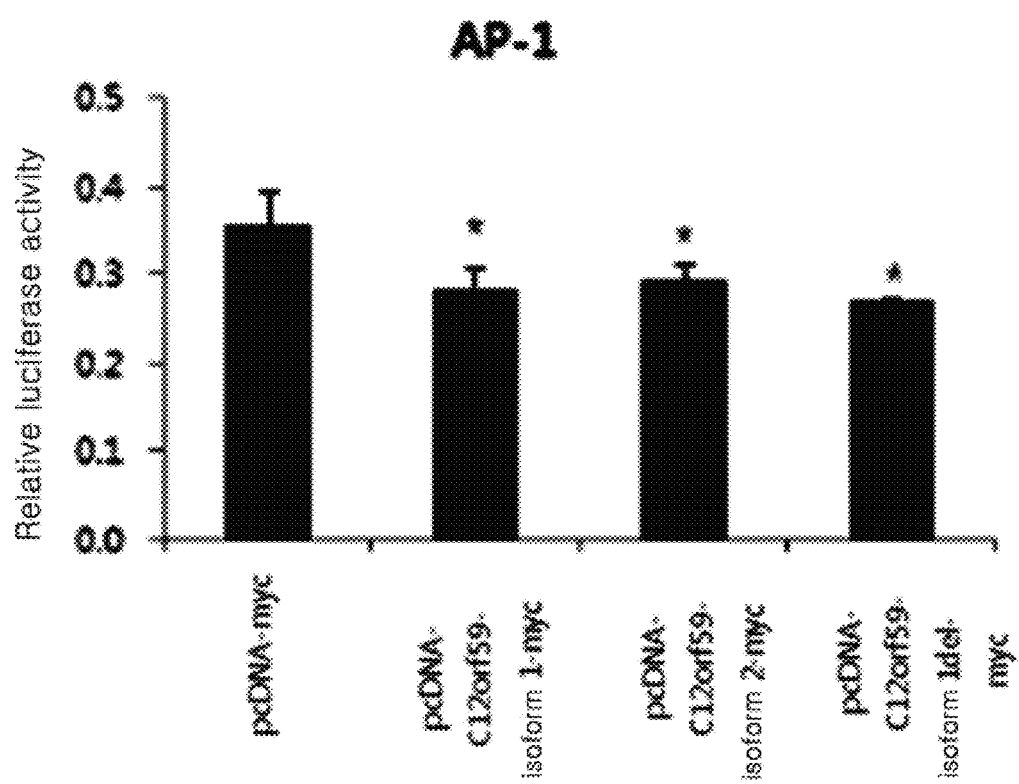
FIG. 6a illustrates the changes of promoter activity of AP-1 cis element after over-expressing C12orf59 protein in SW480 cell line ($*p<0.05$).
Figure 7A:
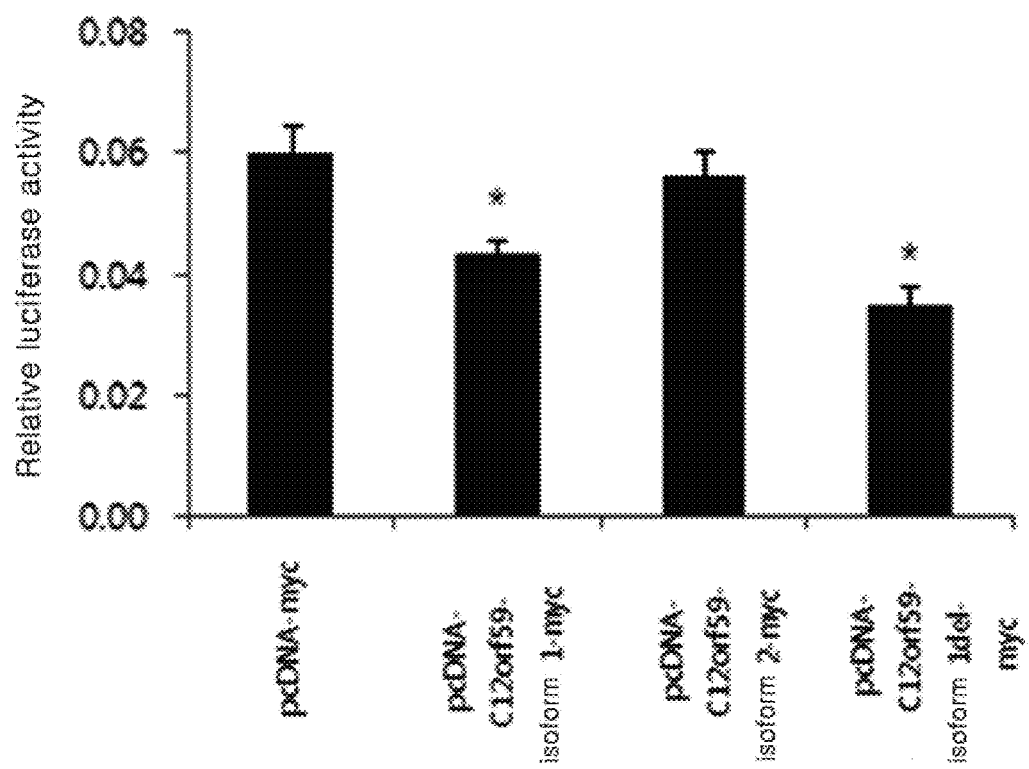
FIG. 7a illustrates the AP-1 activity changes induced by the over-expression of C12orf59 protein in HCT-15 cell line transfected with pcDNA-myc and the C12orf59 protein over-expression vectors pcDNA-C12orf59-isoform1-myc, pcDNA-C12orf59-isoform2-myc, and pcDNA-C12orf59-isoform1del-myc ($*p<0.05$).

As a result, in the cell line introduced with C12orf59 protein, AP-1 cis element and ITGA5 promoter altogether, the activities of AP-1 cis element and ITGA5 promoter were inhibited by C12orf59 over-expression and the inhibition was most peculiar with the vector pcDNA-C12orf59-isoform1del-myc (FIGS. 6a and 6b).

The colon cancer cell line HCT-15 was also transfected with pcDNA-myc, pcDNA-C12orf59-isoform1-myc, pcDNA-C12orf59-isoform2-myc, pcDNA-C12orf59-isoform1del-myc, and AP-1 cis element (AP-1 cis-Reporting system, Stratagene) reporter vector by using LIPOFECTAMINE 2000 reagent by the same manner as described above. 48 hours after the transfection, the activity of AP-1 cis element promoter was confirmed by luciferase assay.

Figure 7B:
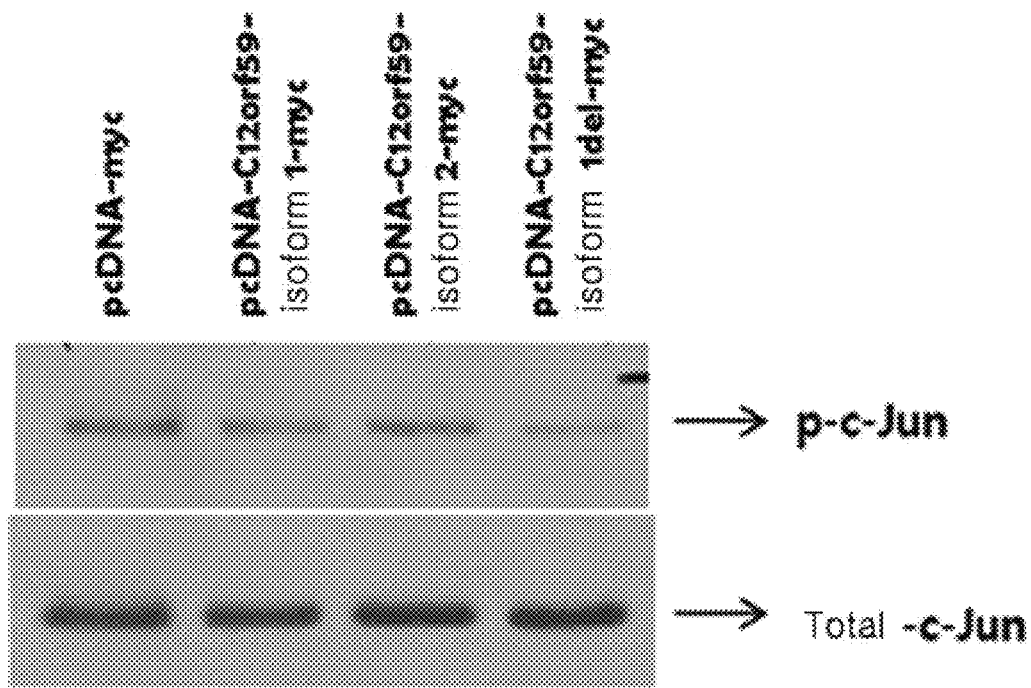
FIG. 7b illustrates the result of Western blotting investigating the AP-1 activity change in HCT-15 cell line over-expressing C12orf59 protein.
Figure 7C:
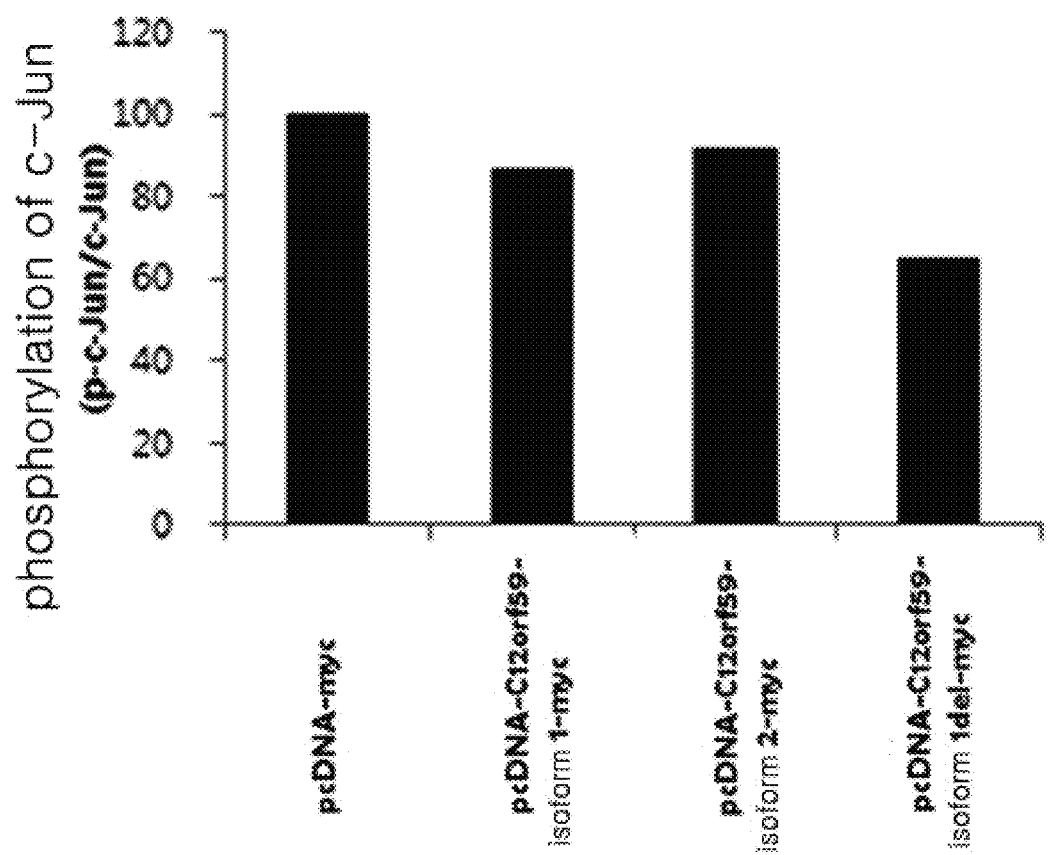
FIG. 7c illustrates the result of densitometry investigating the AP-1 activity change in HCT-15 cell line over-expressing C12orf59 protein.

As a result, it was confirmed that the activity of the transcription factor AP-1 was reduced in HCT-15 cell line by the expression of C12orf59 (FIG. 7a) and the phosphorylation level of c-jun, one of major components of AP-1, was also reduced (FIGS. 7b and 7c).

From the above results, it was confirmed that the inhibition of cell invasion by C12orf59 in cancer cell line was attributed to the suppression of the transcription factor AP-1 activity and the inhibition of integrin α 5 expression.

Experimental Example 2: Inhibition of C12orf59 Expression in Cancer Cell Line

<2-1> Changes of Cell Morphology in Cancer Cell Line by the Inhibition of C12orf59 Expression To investigate the relation of the inhibition of C12orf59 expression and morphological changes in cancer cell line, the colon cancer cell line SW480 was transfected with C12orf59 specific siRNA by electroporation, followed by observation of changes in C12orf59 expression and cell morphology in the cancer cell line.

Particularly, SW480 cells were harvested, followed by washing with PBS. The cells were resuspended in R buffer at the density of $3 \times 10^5$ cells/12 μl, to which 2 μl of 40 μM siRNA was added, followed by transfection using electroporation (NEON Transfection System, Invitrogen). To confirm the inhibition of the expression, RT-PCR was performed. At this time, the C12orf59 specific siRNA was purchased from Dharmacon Co. (4 different mixtures) and the 4 target sequences are as shown in the below:

(SEQ. ID. NO: 7)
5'-GGG UAC AUC UCU GGU AUA U-3', (SEQ. ID. NO: 8)
5'-UCA CAU CUC UGC AGU CGG U-3', (SEQ. ID. NO: 9)
5'-GAA UAG UUG ACU CUU GGA A-3',
and (SEQ. ID. NO: 10)
5'-GGU UCU UAC UCU UCG UUC A-3'.

Cell morphology was observed 48 hours after the transfection with C12orf59 siRNA. Cell shape was observed and photographed under Olympus microscope at 100×. Photographs were compared and analyzed.

Figure 8A:
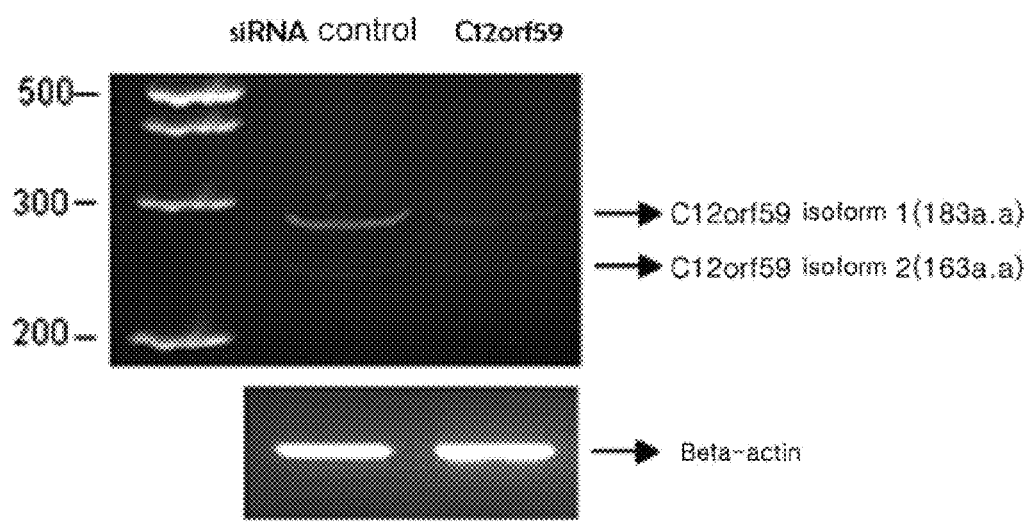
FIG. 8a illustrates the result of electrophoresis confirming the expression of C12orf59 gene in SW480 cell line introduced with C12orf59 siRNA.
Figure 8B:
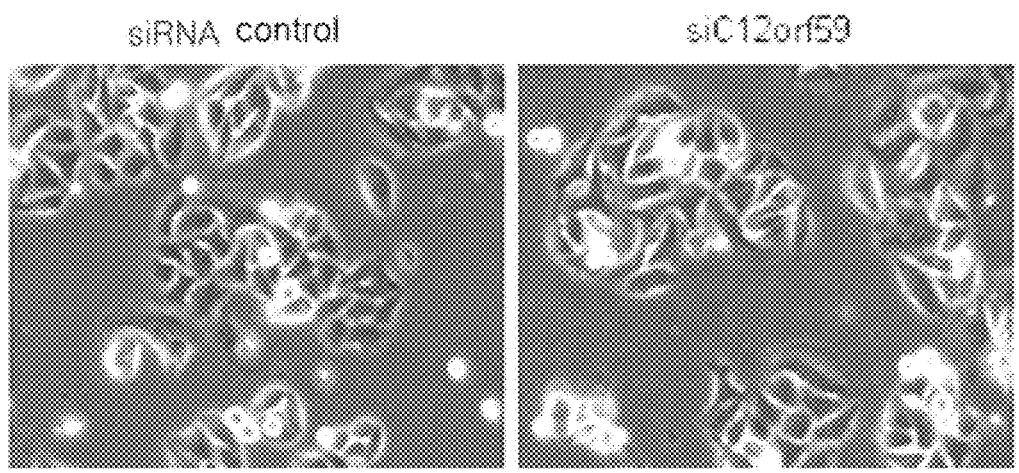
FIG. 8b illustrates the changes of cell morphology in SW480 cell line introduced with C12orf59 siRNA.
Figure 8C:
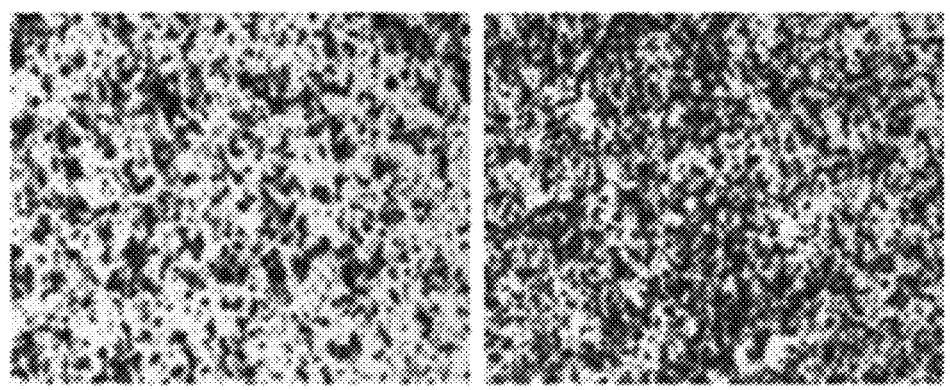
FIG. 8c illustrates the result of cell invasion analysis with SW480 cell line introduced with C12orf59 siRNA (up: representative photograph; down: comparison result after counting).
Figure 8C:
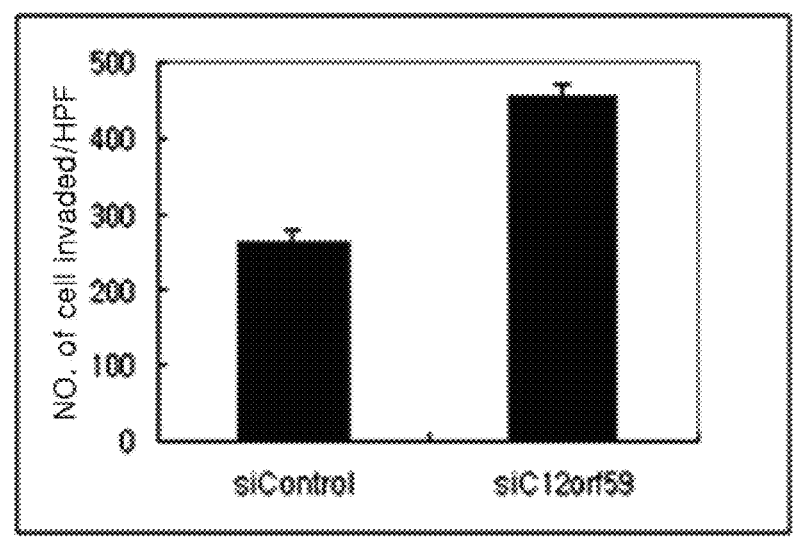

As a result, it was confirmed that the expression of C12orf59 was inhibited 48 hours after the introduction of C12orf59 specific siRNA (Dharmacon) in SW480 cell line (FIG. 8a). Morphological changes like cell diffusion and the formation of lamellipodia were also observed (FIG. 8b).

Therefore, it was confirmed that the expression of C12orf59 in cancer cell line was inhibited by C12orf59 specific siRNA and the inhibition of C12orf59 expression resulted in the changes in cancer cell morphology into the typical form that was highly apt to migrate.

<2-2> Cancer Cell Invasion Ability Affected by the Inhibition of C12orf59 Expression in Cancer Cell Line To analyze cancer cell invasion ability affected by the inhibition of C12orf59 expression in cancer cell line, SW480 cell line was transfected with C12orf59 specific siRNA (Dharmacon) and the control siRNA (sense strand: 5'-CUU ACG CUG AGU ACU UCG ATT-3' (SEQ. ID. NO: 11), anti-sense strand: 5'-UCG AAG UAC UCA GCG UAA GTT-3' (SEQ. ID. NO: 12), Samchully Pharmaceutical Co. Ltd., Korea), followed by invasion assay 48 hours later.

Particularly, the porous membrane of 24-well transwell plate (8 μm pore size; Costar, USA) was coated with 100 μm of matrigel (BD Biosciences, USA) diluted in serum free medium at the concentration of 250 μg/ml, which stood at room temperature for 1 hour for fixing. The lower part of the transwell plate was coated with 100 μl of collagen type I (Sigma) at the concentration of 20 μg/ml. The said collagen type I was used as a chemoattractant. $3 \times 10^4$ SW480 cells resuspended in serum free medium were distributed in the upper chamber of the said 24-well transwell plate, followed by culture at 37° C. with 5% $CO_2$ for 48 hours, during which the cells were induced to migrate from the upper chamber to the lower chamber. The non-migrated cells were eliminated from the surface of the upper chamber. The cells migrated to the lower chamber were fixed with 3.7% paraformaldehyde dissolved in PBS, followed by staining with 2% crystal violet solution. The excessive crystal violet solution was washed off with distilled water. The selected area (×200) was photographed. The number of the cells migrated was counted from 5 different selected areas. The experiment was duplicated with the same condition to make sure the results. Data reflected migrated cells±standard error at ×200 HPF (high power field).

As a result, the inhibition of C12orf59 expression resulted in the increase of cancer cell invasion (FIG. 8c), indicating that the inhibition of C12orf59 expression in cancer cell line induced cancer cell morphological changes, increased cell migration, and hence increased cancer cell invasion ability.

Figure 9A:
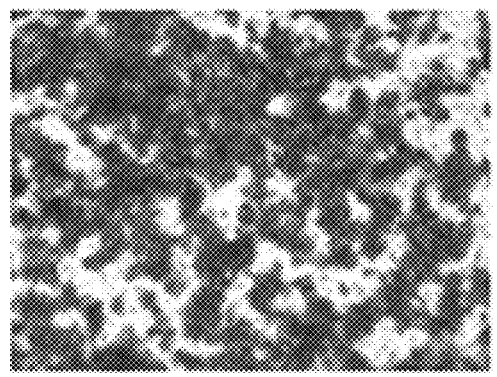
FIG. 9a illustrates the changes of cancer cell invasion measured by using HCT-15 cell line introduced with C12orf59 siRNA.
Figure 9A:
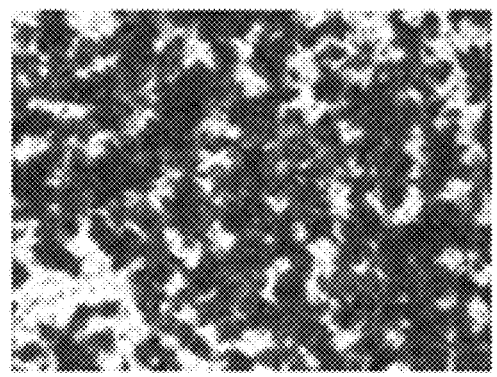
Figure 9B:
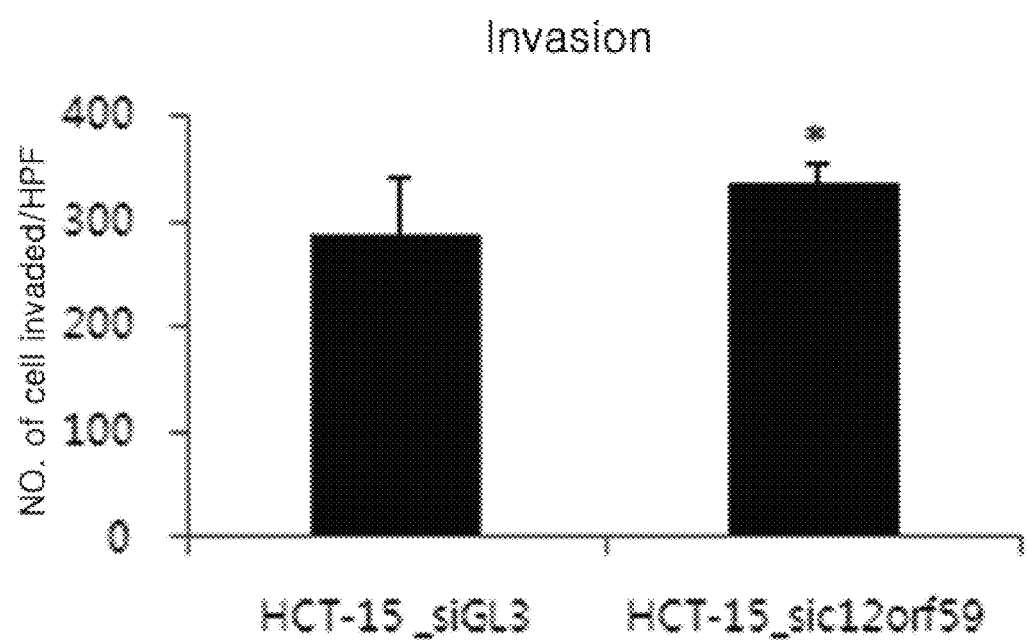
FIG. 9b illustrates the result of counting the invaded cancer cells after suppressing the expression of C12orf59 in HCT-15 cell line ($*p<0.05$).

The colon cancer cell line HCT-15 was also transfected with C12orf59 specific siRNA (Samchully Pharmaceutical Co. Ltd., Korea) by microporation. 48 hours later, the experiment using collagen and transwell coated with matrigel was performed by the same manner as described above. As a result, it was confirmed that cancer cell invasion was increased by the inhibition of C12orf59 expression in HCT-15 cell line (FIGS. 9a and 9b).

<2-3> Investigation of Cancer Cell Survivability Affected by the Inhibition of C12orf59 Expression in Cancer Cell Line To investigate whether or not the inhibition of C12orf59 expression could affect cancer cell survivability, cell survival rate was measured under the anchorage independent condition.

Particularly, 100 μl of poly-HEMA (Sigma) at the concentration of 12 mg/ml was loaded in 96-well plate, which stood in clean bench for 1 day, followed by drying. On the next day, the plate was coated with Poly-HEMA once again. SW480 cancer cells were transfected with siRNA for 48 hours, the cells were diluted at the density of $1 \times 10^4$, followed by plating in each well by 100 μl. At that time, serum free medium was used. 72 hours later, 10 μl of CCK-8 reagent (Dojindo cat. CK04-13) was added to each well, followed by reaction for 3 hours to induce color development. Then, $OD_{450}$ was measured to investigate cell survivability.

Figure 10:
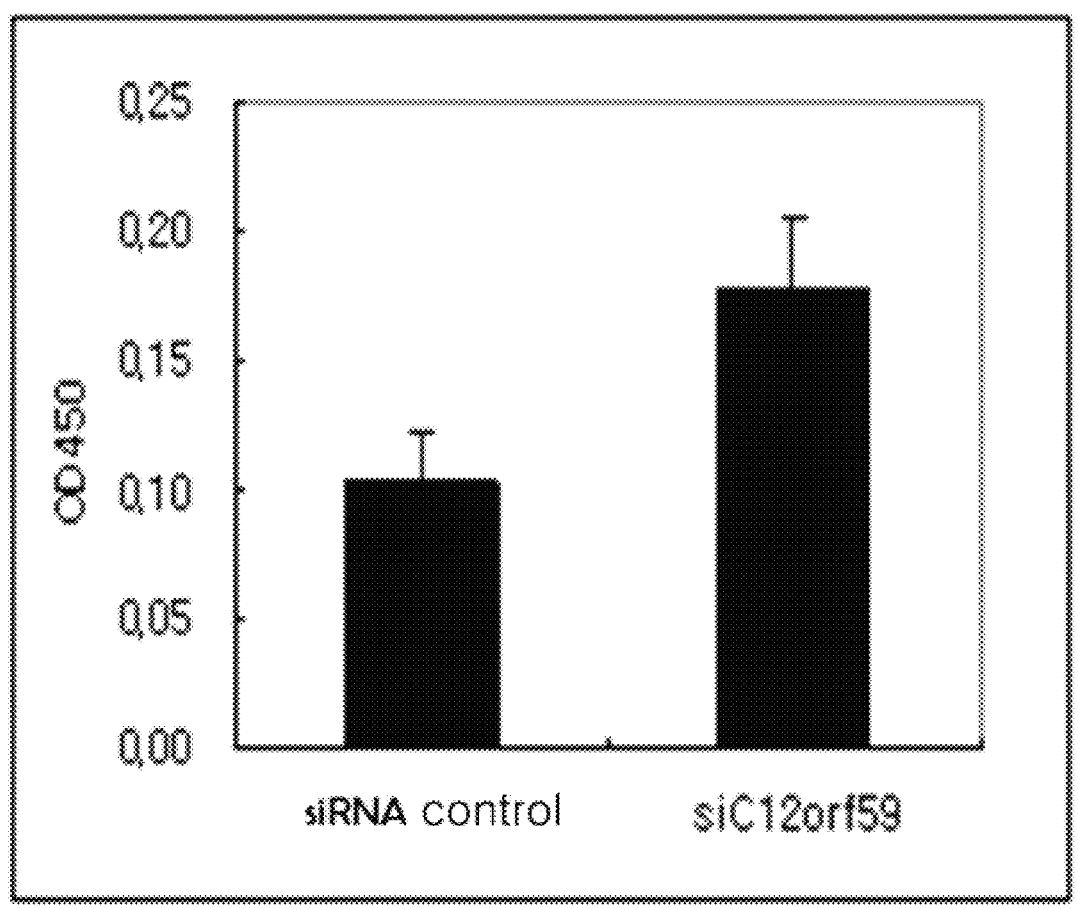
FIG. 10 illustrates the cell survivability of SW480 cell line introduced with C12orf59 siRNA.

As a result, it was confirmed that cancer cell survivability was increased when C12orf59 siRNA was treated to inhibit the expression of C12orf59, compared with when the control siRNA was treated (FIG. 10). Therefore, it was confirmed that the inhibition of C12orf59 expression induced anoikis (apoptosis following loss of cell anchorage)-resistance.

<2-4> Activation of Signal Transmission Pathway by the Inhibition of C12orf59 Expression in Cancer Cell Line To investigate the activation of cell signal transmission pathway by C12orf59 siRNA in cancer cell line, the colon cancer cell line SW480 was transfected with C12orf59 specific siRNA. 48 hours later, the cell lysate was obtained, and Western blotting was performed using the same.

Particularly, the cells were lysed with RIPA buffer (10 mM Tris, pH7.2, 150 mM NaCl, 1% deoxycholate, 1% Triton X-100, 0.1% SDS, 1 mM sodium orthovanadate, 50 mM NaF, 1 mM PMSF, complete protease inhibitor) and the cell lysate was quantified by modified Bradford assay (Bio-Rad Laboratories, Hercules, Calif.). 30 μl of the obtained cell lysate was mixed with SDS sample buffer, which was heated, followed by electrophoresis on 8% SDS-PAGE gel. The protein isolated on SDS-PAGE gel through electrophoresis was transferred onto nitrocellulose membrane, followed by blocking with 5% skim milk. The membrane was reacted with anti-beta-actin antibody (1:1000, Santa Cruz), anti-phosphorylated-ERK1/2 antibody, anti-ERK1/2 antibody, anti-phosphorylated-p38 antibody, anti-p38 antibody, anti-phosphorylated-JNK antibody, and anti-JNK antibody (1:1000, Cell signaling technology) as primary antibodies. Then, the membrane was reacted with horseradish peroxidase-conjugated secondary antibody, followed by color development by using ECL kit (ECL Plus, Amersham, USA) according to the manufacturer's instruction.

As a result, it was confirmed that the phosphorylations of ERK1/2, p38, and JNK were all increased by the inhibition of C12orf59 expression (FIG. 11), suggesting that MAPK activation contributed to cancer cell invasion and cancer cell survivability induced by the inhibition of C12orf59 expression.

Experimental Example 3: Effect of the A_Intact Peptide and the B_Intact Peptide, which are Originated from C12orf59 Isoform, on Cancer Cells <3-1> Inhibition of Colorectal Cancer Cell Invasion by A_Intact Peptide and B_Intact Peptide Inhibitory effect of the peptide prepared in Example 6 on colorectal cancer cell invasion was investigated.

SW480sub was subpopulation of SW480 having high in vitro invasion and in vivo metastasis ability. The effect of each peptide on colorectal cancer cell invasion was analyzed using the said SW480sub. SW480sub cells were mixed with each peptide, followed by pre-incubation for 30 minutes. The cell/peptide mixture was then distributed in the upper chamber of transwell plate, while buffer was added to the lower chamber, followed by invasion assay.

Particularly, the porous membrane of 24-well transwell plate (8 μm pore size; Costar, USA) was coated with 100 μl of matrigel (BD Biosciences, USA) diluted in serum free medium at the concentration of 250 μl/ml, which stood at room temperature for 1 hour for fixing. The lower part of the transwell plate was coated with 100 μl of collagen type I (Sigma) at the concentration of 20 μl/ml. The said collagen type I was used as a chemoattractant. $1\times10^4$ cells resuspended in serum free medium were distributed in the upper chamber of the said 24-well transwell plate, followed by culture at 37° C. with 5% $CO_2$ for 48 hours, during which the cells were induced to migrate from the upper chamber to the lower chamber. The non-migrated cells were eliminated from the surface of the upper chamber. The cells migrated to the lower chamber were fixed with 3.7% paraformaldehyde dissolved in PBS, followed by staining with 2% crystal violet solution. The excessive crystal violet solution was washed off with distilled water. The selected area (×100) was photographed. The number of the cells migrated was counted from 5 different selected areas. Then, mean value and standard error were obtained.

Figure 12:
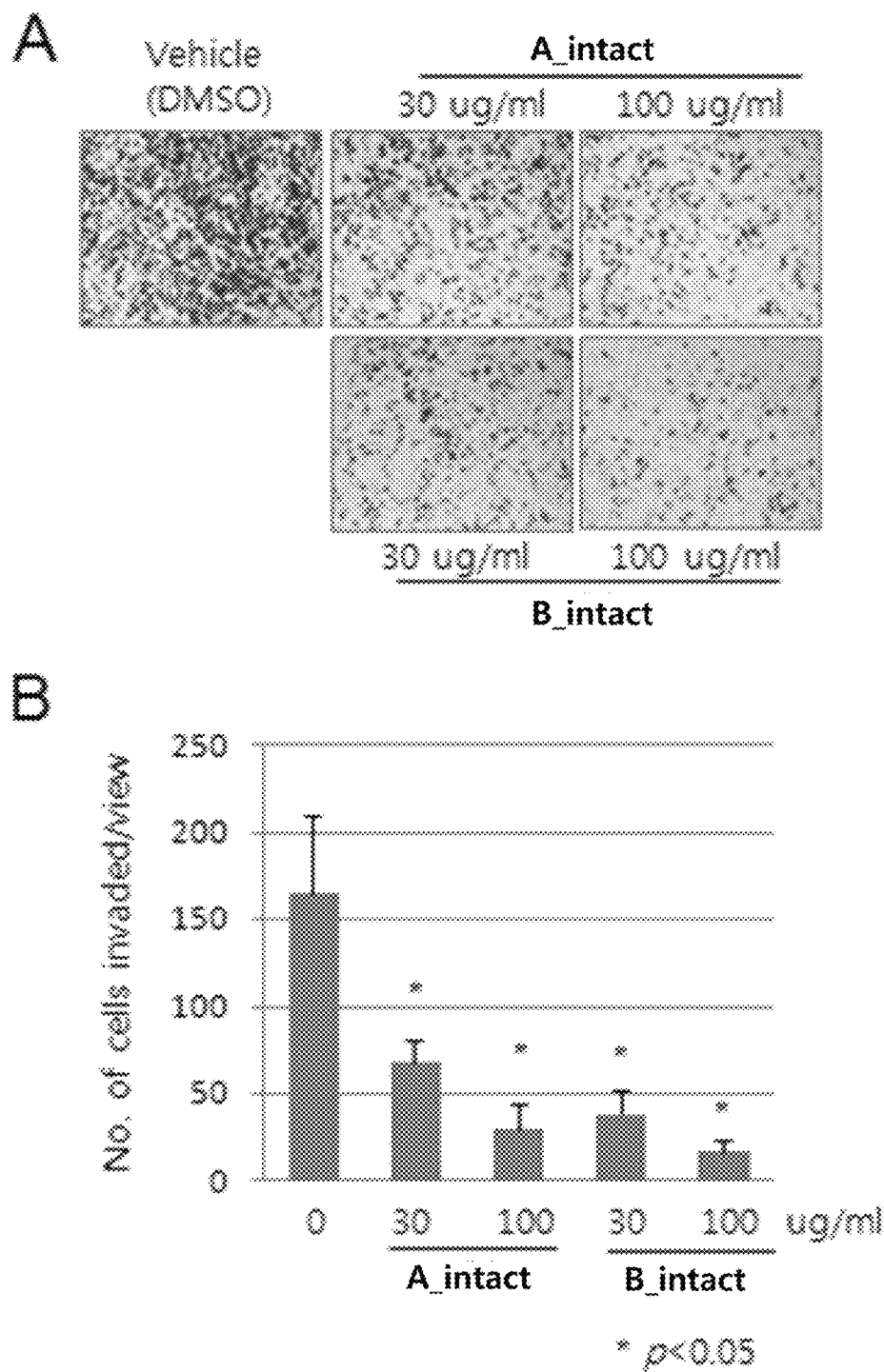
FIG. 12 is a diagram illustrating the inhibitory effect of the peptide of the present invention on the colorectal cancer cell invasion.
  A: representative photograph;
  B: mean value and standard deviation.

As a result, as shown in FIG. 12, colorectal cancer cell invasion was reduced by 82% and 90% by A_intact and B_intact (100 μg/ml) respectively (FIG. 12).

<3-2> Effect of the A_Intact and B_Intact Peptides on Colorectal Cancer Cell Survivability To investigate the effect of the peptide prepared in Example 6 on colorectal cancer cell survivability, SW480 cells were mixed with each peptide and then distributed in 96-well plate coated with polyHEMA. 6 days later, cell survivability was measured by colorimetric technique under the anchorage independent condition.

Particularly, 100 μl of poly-HEMA (Sigma) at the concentration of 12 mg/ml was loaded in 96-well plate, which stood in clean bench for 1 day, followed by drying. On the next day, the plate was coated with Poly-HEMA once again. Cells were distributed in the poly-HEMA coated plate by 100 μl/well ($1\times10^4$ cells/well). At that time, serum-free medium was used. 6 days later, 10 μl of CCK-8 reagent (Dojindo cat. CK04-13) was added to each well, followed by reaction for 3 hours. Then, $OD_{450}$ was measured.

Figure 13:
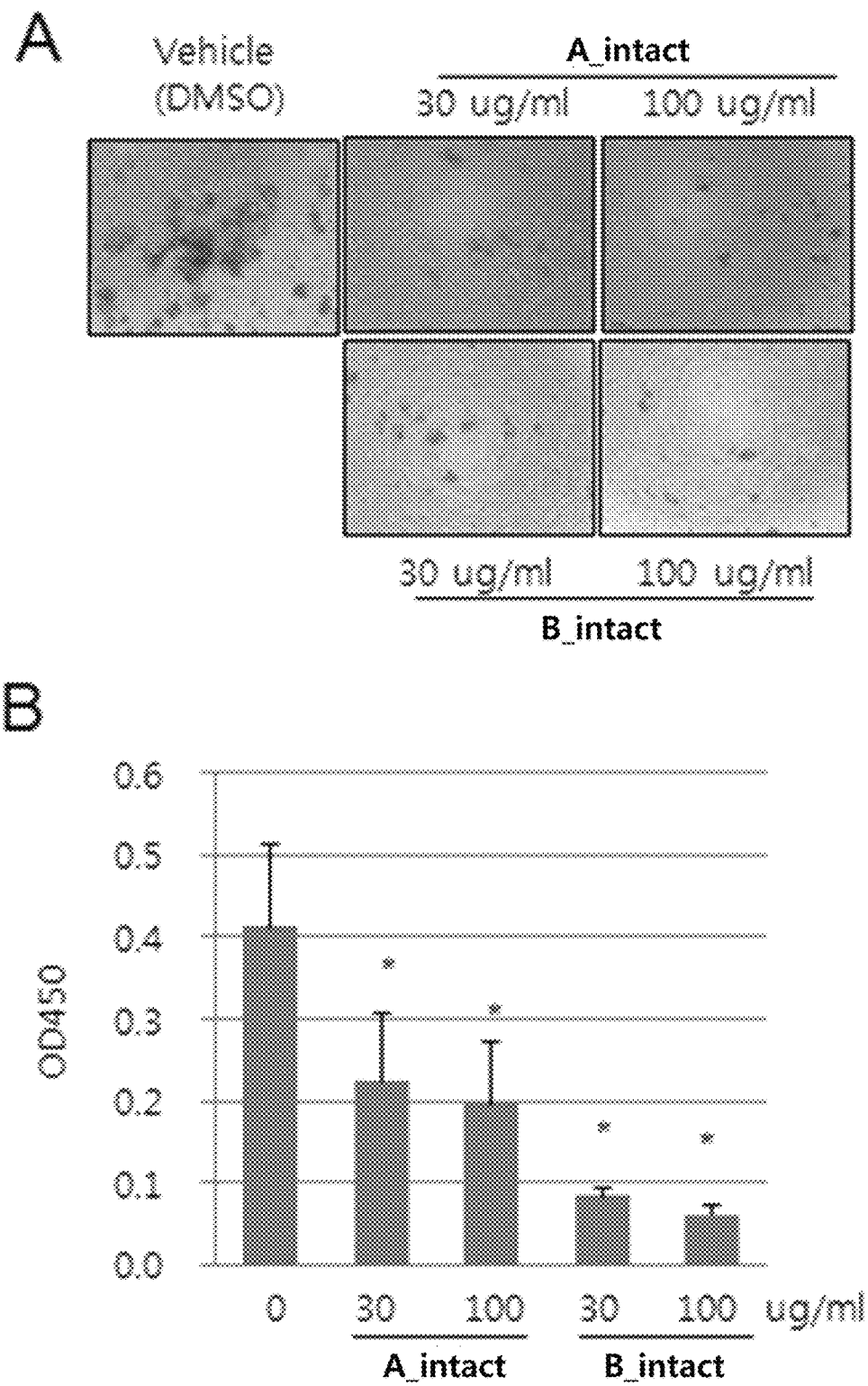
FIG. 13 is a diagram illustrating the changes of colorectal cancer cell survivability by the treatment of the peptide of the present invention.
  A: representative photograph;
  B: OD values.

As a result, as shown in FIG. 13, cell survivability was reduced by 82% and 90% by A_intact and B_intact (100 μl/ml) respectively (FIG. 13).

<3-3> Effect of Peptides Originated from C12orf59 Isoforms on Invasion of SW480sub Cells From Experimental Examples <3-1> and <3-2>, it was confirmed that A_intact peptide and B_intact peptide exhibit effects on cancer cell invasion. Accordingly, it was decided to develop a peptide which is capable of effectively inhibiting cancer cell invasion while having a shorter length compared to A_intact or B_intact peptides. Therefore, SW480sub cells were treated with each of the peptides of SEQ. ID. NOS: 30 to 39 prepared in Example 6, and cell invasion was analyzed.

In particular, in order to investigate an effect of A_intact, A_C-term1, A_C-term2, B_intact, B_C-term1, B_Cen, and B_C-term2 which are peptides originated from C12orf59 prepared in Example 6 on an invasion ability of SW480sub cells cultured according to Example 1, invasion assay was performed as described in Example <3-1>. The peptides used therein were treated on cells at a concentration of 50 μM, except B_intact peptide which had a concentration of 43 μM.

Figure 14:
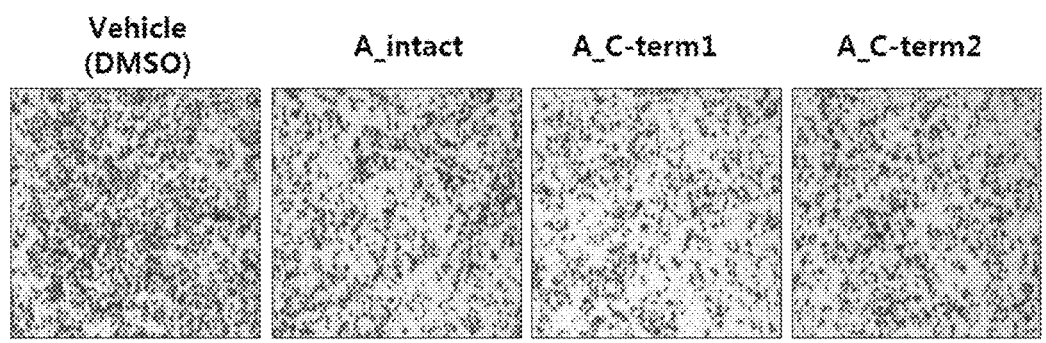
FIG. 14 illustrates the result of cell invasion analysis after treating SW480sub cells with A_intact, A_C-term1, and A_C-term2 peptides.
Figure 14:
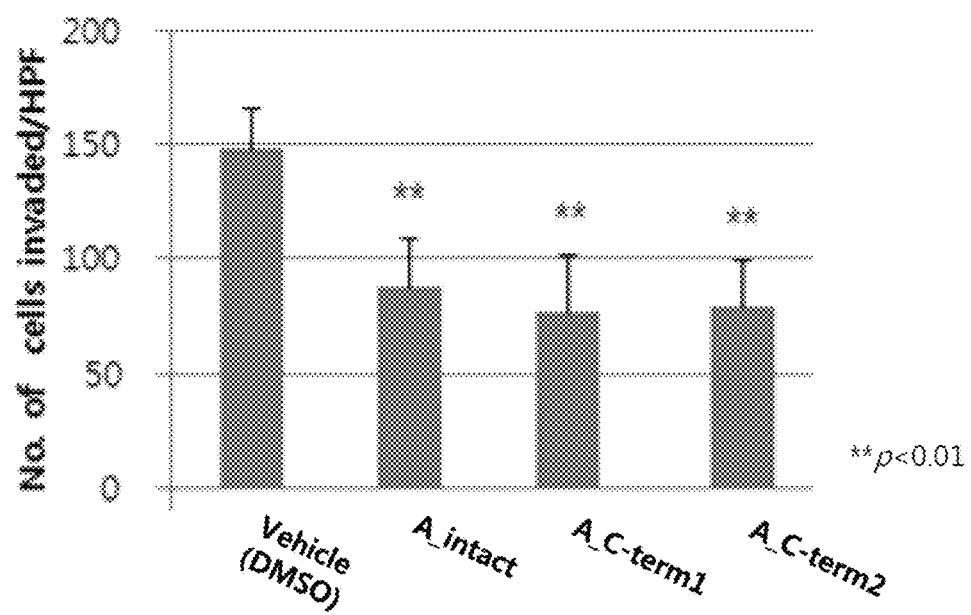
Figure 15:
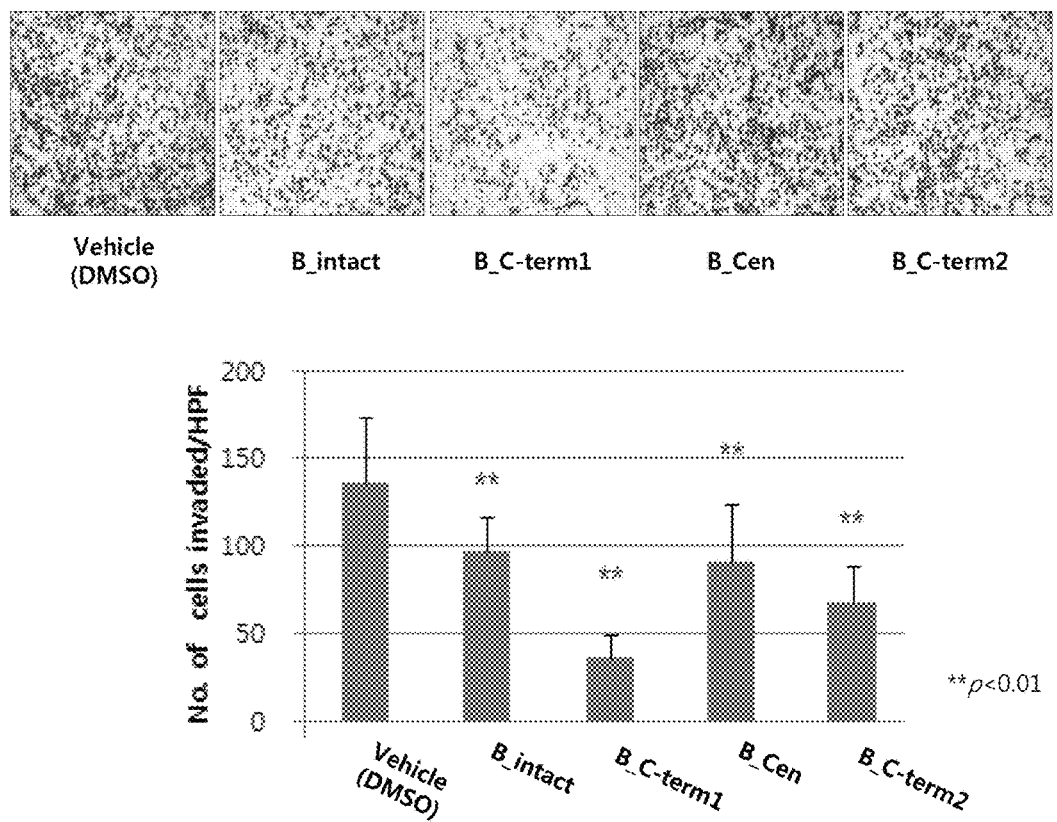
FIG. 15 illustrates the result of cell invasion analysis after treating SW480sub cells with B_intact, B_C-term1, B_Cen, and B_C-term2 peptides.

Through a microscope, the results confirmed that invasion was reduced when 7 peptides originated from C12orf59 peptides was treated, as demonstrated in FIGS. 14 and 15.

It was observed that invasion of colorectal cancer cells were significantly reduced by in the order of 40%, 48% and 46% due to A_intact, A_N-term, A_C-term1, A_Cen, and A_C-term2 peptides compared to that of the vehicle control.

Additionally, the invasion rate was significantly reduced by in the order of 29%, 73%, 33%, and 50% due to B_intact, B_C-term1, B_Cen, and B_C-term2 peptides compared to the control. Compared to the antecedent peptide, A_intact and B_intact, A_C-term1, A_C-term2, B_C-term1, B_Cen, and B_C-term2 exhibited similar or superior effects on invasion of colorectal cancer cells, despite their shorter length.

Figure 16:
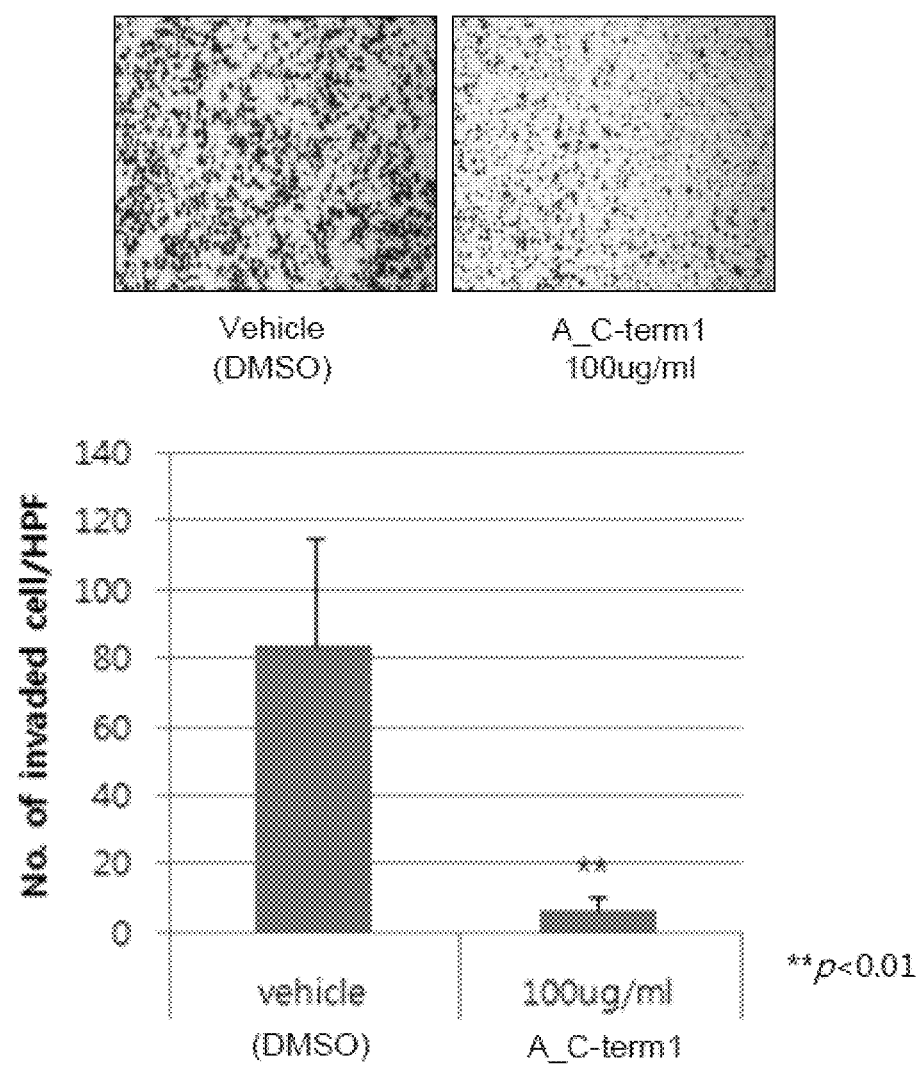
FIG. 16 illustrates the result of cell invasion analysis after treating SW480sub cells with A_C-term1 peptide at a concentration of 100 μg/mL.
Figure 17:
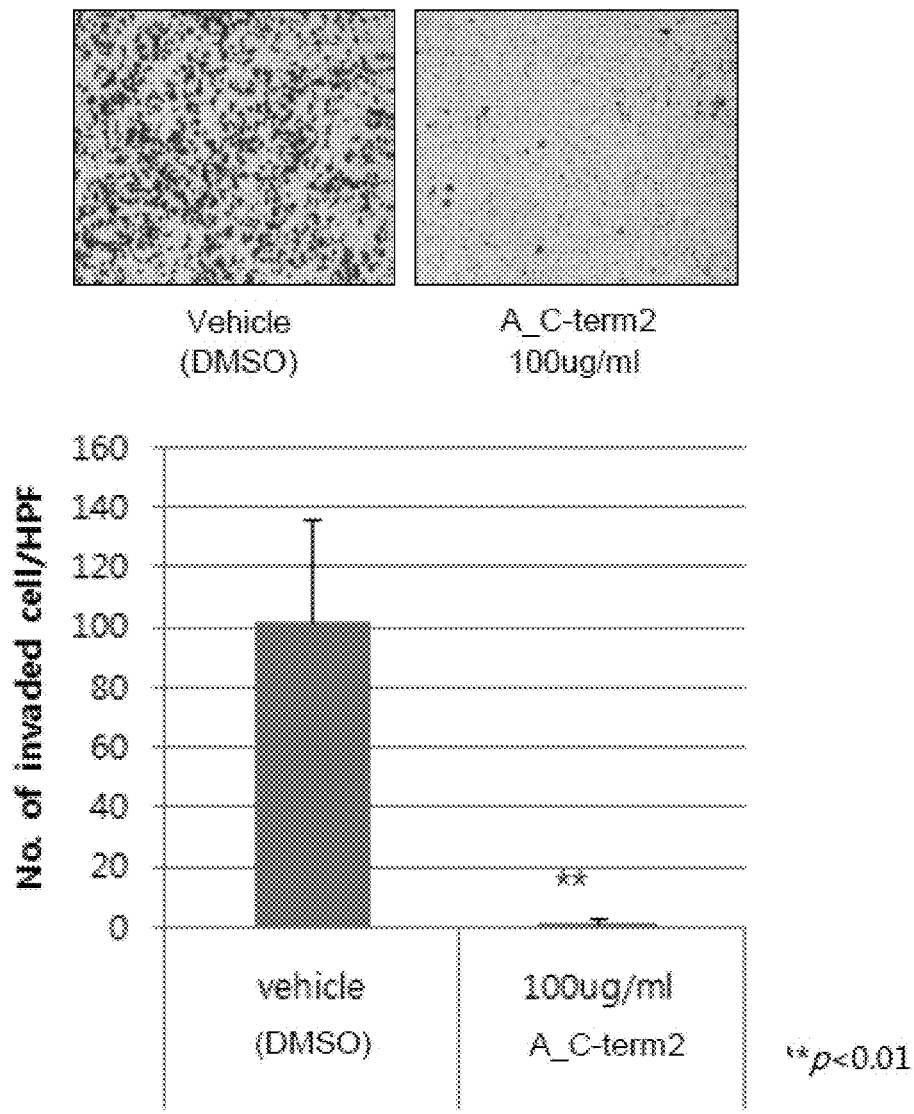
FIG. 17 illustrates the result of cell invasion analysis after treating SW480sub cells with A_C-term2 peptide at a concentration of 100 μg/mL.

In addition, the effect of the peptides on cancer cell invasion was investigated by treating SW480sub cells with A_C-term1 and A_C-term2 each at a concentration of 100 μg/mL, and the results are demonstrated in FIGS. 16 and 17.

As demonstrated in FIGS. 16 and 17, the results showed that compared to the vehicle group treated with DMSO, the treatment of A_C-term1 and A_C-term2 peptides according to the present invention effectively inhibited the invasion of colorectal cancer cells. Especially, compared to treating A_intact peptide at an identical concentration (100 μg/mL) of A_C-term1 and A_C-term2 peptides as demonstrated in FIG. 12, treating A_C-term1 and A_C-term2 peptides exhibited greater inhibitory effects on colorectal cancer invasion while having a shorter length, as A_C-term1 exhibited inhibitory effects of about 92%, and A_C-term2 exhibited inhibitory effects of about 99%, while A_intact exhibited inhibitory effects of about 82%.

<3-4> Effect of Peptides Originated from C12orf59 Isoforms on Invasion of SW480 Cells SW480 colorectal cancer cells were treated with peptides originated from C12orf59, and effects of the peptides on invasion of the cells were analyzed.

In particular, in order to investigate the effect of 8 kinds of peptides originated from C12orf59 prepared in Example 6 on invasion of SW480 cells cultured according to Example 1, invasion assay was performed in the same manner as described in Example <3-2>.

Figure 18:
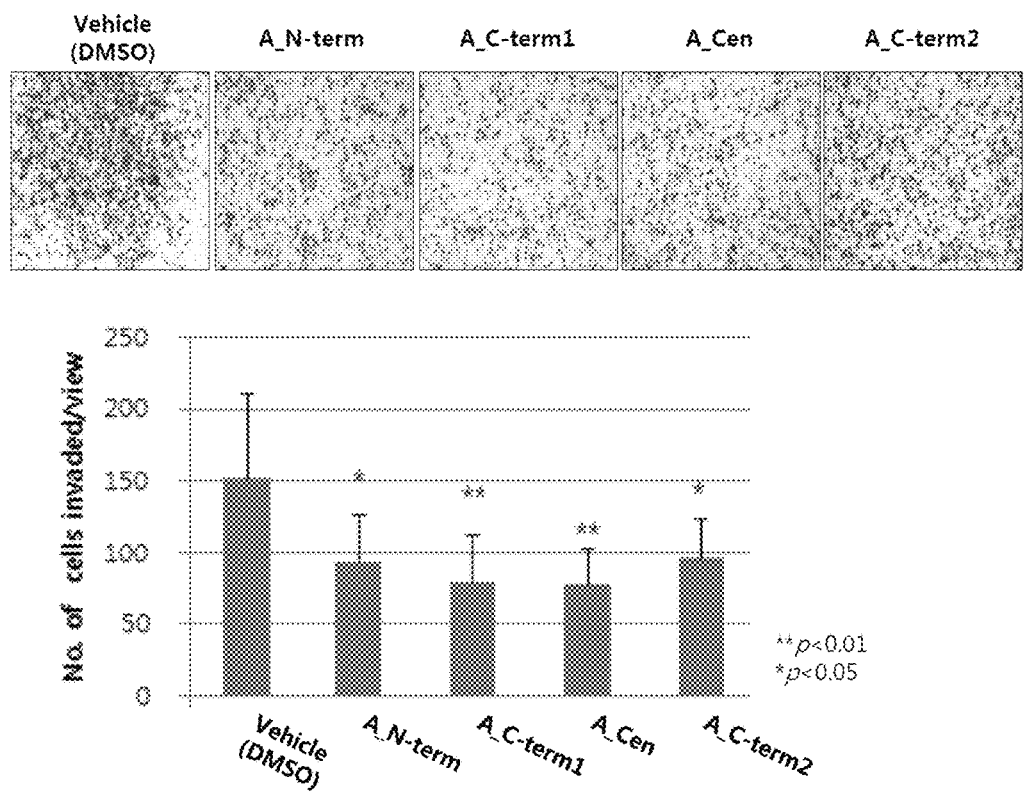
FIG. 18 illustrates the result of cell invasion analysis after treating SW480 cell with A_N-term, A_C-term1, A_Cen, and A_C-term2 peptides.
Figure 19:
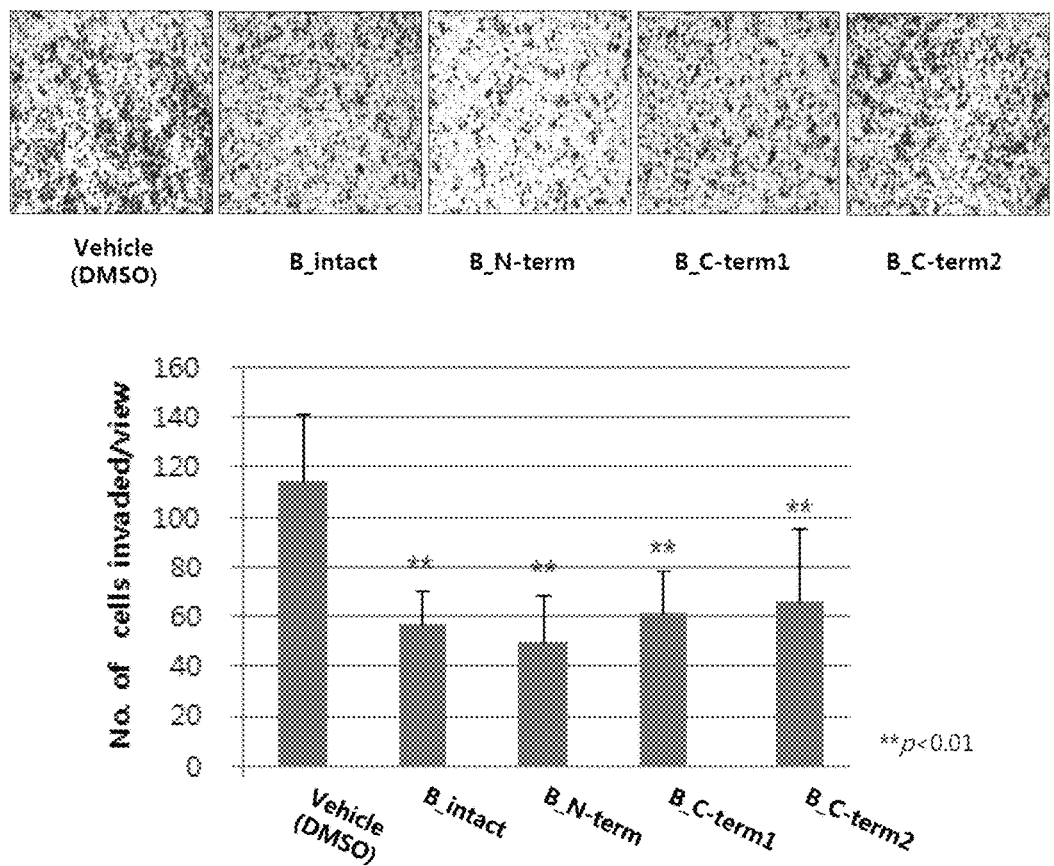
FIG. 19 illustrates the result of cell invasion analysis after treating SW480 cell with B_intact, B_N-term, B_C-term1, and B_C-term2 peptides.

Through a microscope, the results confirmed that a total of 8 kinds of peptides originated from C12orf59 reduced cancer cell invasion, as demonstrated in FIGS. 18 and 19.

Quantitatively, it was observed that the invasion of cells was reduced by 39%, 48%, 49%, and 38% by A_N-term, A_C-term1, A_Cen, and A_C-term2 peptides, respectively (FIG. 18).

Additionally, the invasion rate was reduced by 47%, 55%, 45%, and 39% by B_intact, B_N-term, B_C-term1, and B_C-term2 peptides, respectively (FIG. 19).

<3-5> Effect of Peptides A/B Common and B_Cen2 on Invasion of SW480 Cells

In order to investigate effects of A_C-term2, B_C-term2, A/B common and B_Cen2 peptides prepared in Example 6 on the invasion of colorectal cancer cells, SW480 cells were treated with A_C-term2, B_C-term2, A/B common, and B_Cen2 peptides at a concentration of 50 µM. Further, SW480 cells were treated with DMSO 0.25% to serve as a control. The experiments were performed in the same manner as described in Experimental Example 3-1.

The results showed that all of the four peptides inhibited the invasion of colorectal cancer cells compared to the control. Especially, B_Cen2 exhibited superior inhibitory effects on invasion of colorectal cancer cells even compared to A/B common, A_C-term2, and B_C-term2. A/B common also showed effects similar to those of A_C-term2 and B_C-term2.

Experimental Example 4: Effects of Peptides Originated from C12orf59 on the Survival Rate of Colorectal Cancer Cells Based on the results of Experimental Example <3-2> which showed that the cancer cell survival rate was reduced in SW480sub colorectal cancer cells, the effect of A_N-term, A_C-term1, B_N-term, and B_C-term1 peptides on cellular survival rate was analyzed.

In particular, a cellular survival rate was measured using absorbance in the same manner as in Example <3-2>.

The results showed that A_N-term, A_C-term1, B_N-term, or B_C-term1 peptides all exhibited inhibitory effects on the survival of colorectal cancer cells in a concentration-dependent manner.

Experimental Example 5: In Vivo Metastasis Inhibition by A_Intact Peptide

1. Generation of A_Intact-Fc Fusion Protein

Figure 20:
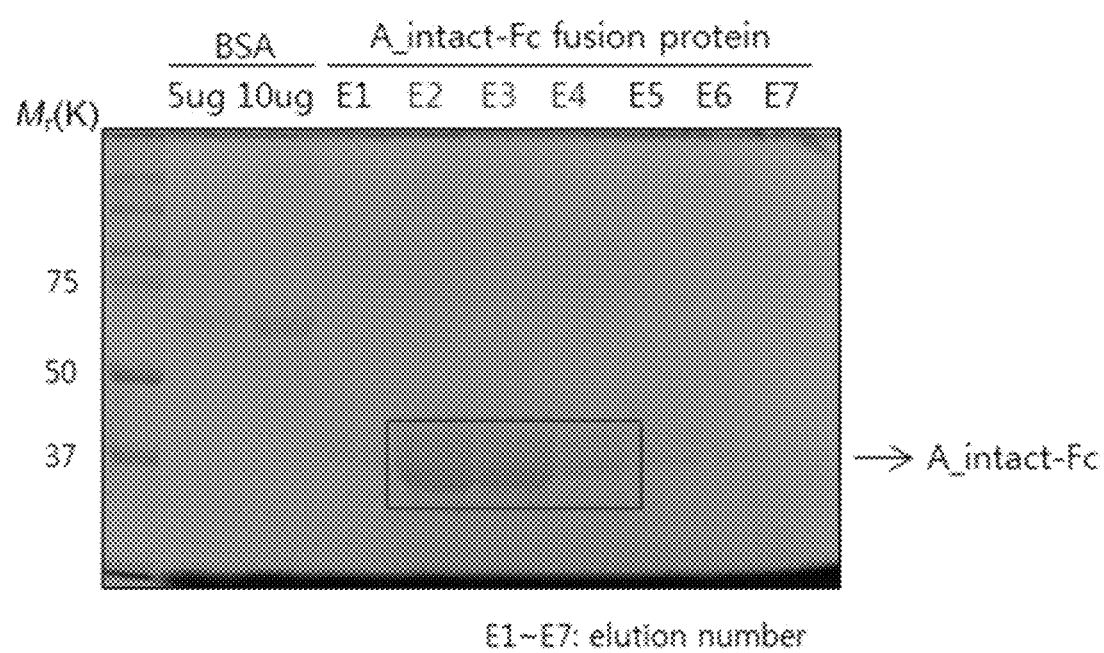
FIG. 20 shows the result of purification of A_intact-Fc fusion protein.

A_intact peptide fused with human immunoglobulin Fc protein was generated and total 4.5 mg was obtained (FIG. 20). N-terminal sequence (EEN) of this fusion protein was confirmed by N-terminal amino acid sequencing analysis service (Cosmogenetech co, Ltd, Seoul, Korea).

2. In Vivo Metastasis Inhibition by A_Intact-Fc Fusion Protein and A_Intact Peptide (1) In Vivo Experimental Metastasis Model In vivo therapeutic efficacy of A_intact peptide was evaluated using experimental metastasis mouse model. The in vivo experimental metastasis model was constructed as described below.

Nude mice (BALB/c-nude, 6 weeks old, female) were obtained from Charles River Japan (Japan). C8161 (human melanoma) cells ($8 \times 10^5$ cells in 1000 PBS per mouse) were injected into the tail vein. Two days later, mice were randomized into control and treatment groups (n=5 per group). Modified A_intact peptide (200 µl/100 µl PBS) or A_intact-Fc fusion protein (100 µl/100 µl PBS) were intravenously injected into each mouse twice per week (total 7 times). As a negative control, PBS (100 µl/mouse) was injected. All animals were killed at 4 weeks after injection of cancer cells. Lung and liver were excised and fixed in 10% formalin for 24 h. Metastatic foci on the surface of lung and liver were counted.

Figure 21A:
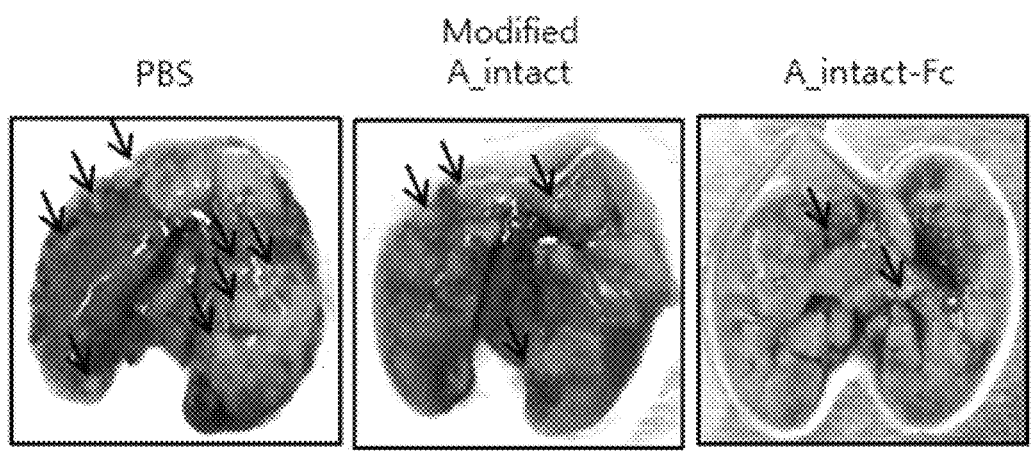
FIGS. 21a and 21b show the effect of a modified A_intact peptide and the A_intact-Fc fusion protein on in vivo metastasis. Metastatic lung (FIG. 21a) and liver (FIG. 21b) nodules were counted and representative photos are shown.
Figure 21B:
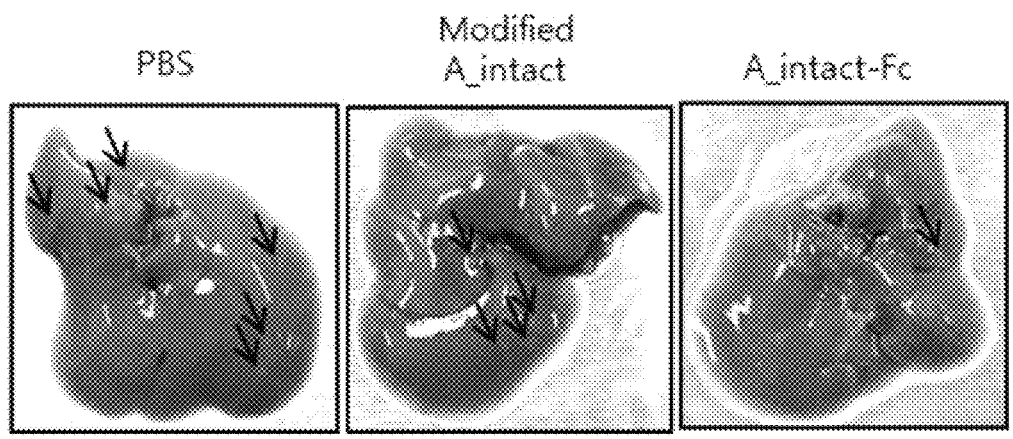

When compared with negative control (PBS), A_intact-Fc fusion protein inhibited metastasis to the lung and liver in nude mice. Modified A_intact peptide (N-terminal acetylation and C-terminal amidation) also inhibited metastasis to the lung and liver in nude mice (FIGS. 21*a* and 21*b*).

(2) Invasion Assay

First, the invasion assay was performed as shown below.

Specifically, C8161 (human melanoma) cell line was cultured in DMEM containing 10% FBS, penicillin-streptomycin, L-glutamine, sodium pyruvate and glucose. C8161 cells ($1 \times 10^4$) in the presence of the peptide were plated in serum-free medium on 24-well Transwell inserts (8 µm pore size; Costar, USA) coated with 25 µg of MATRIGEL (BD Biosciences, USA). The underside of the insert was coated with 100 µl of collagen type I (Sigma) at the concentration of 5 µg/ml. After incubation for 24 h at 37° C. with 5% $CO_2$, the inserts were fixed with 3.7% paraformaldehyde dissolved in PBS, followed by staining with 2% crystal violet solution. The number of cells that had invaded was counted in five representative fields per insert. Then, mean value and standard deviation were obtained. The results are shown in FIG. 22.

Figure 22:
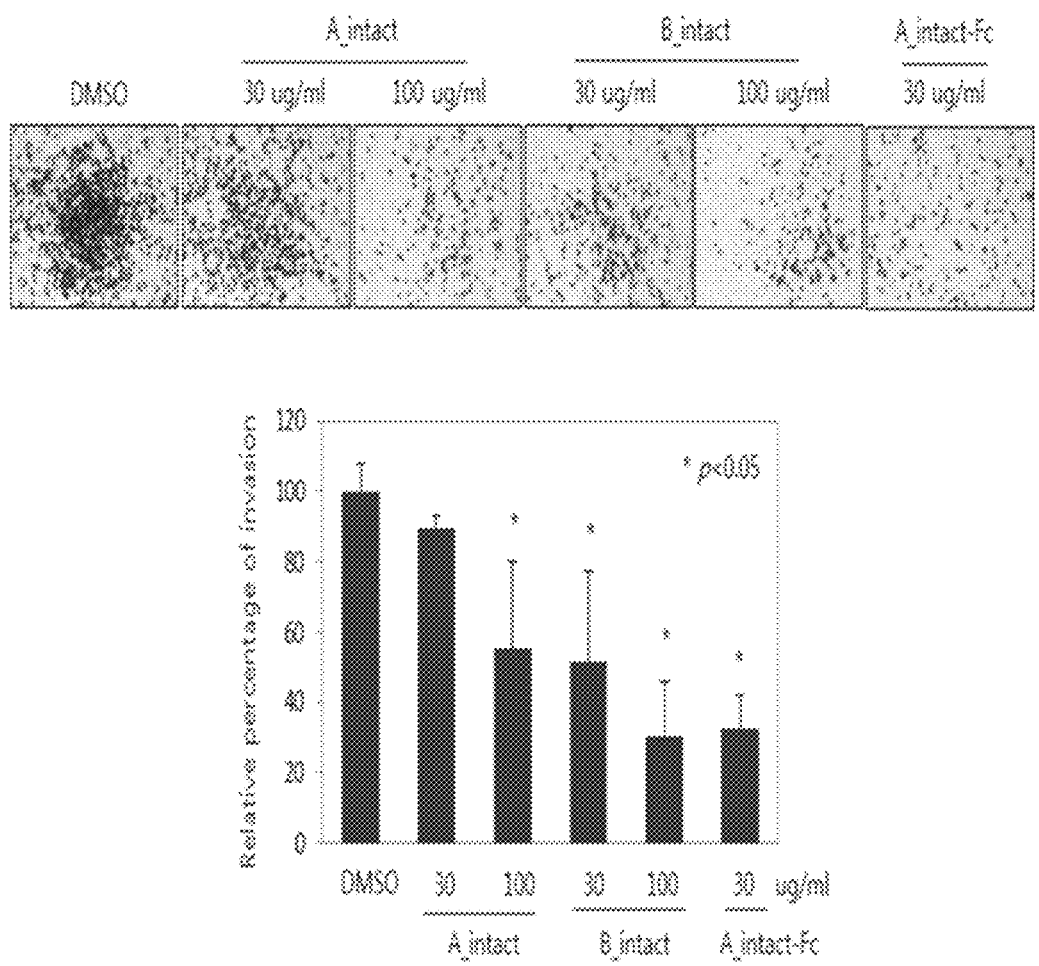
FIG. 22 shows the effect of the modified A_intact peptide and the A_intact-Fc fusion protein on invasion of C8161 cancer cells.
Figure 23:
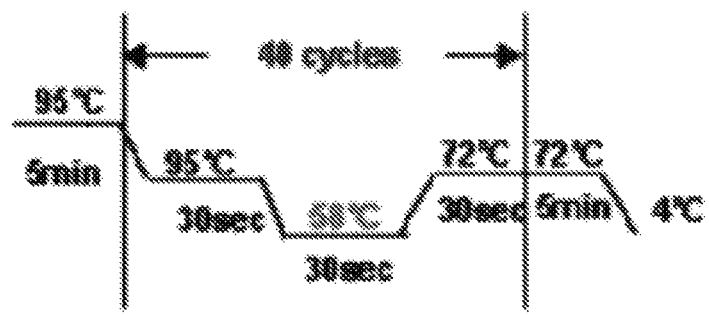
FIG. 23 depicts PCR conditions used with the mixture of Table 1.
Figure 24:
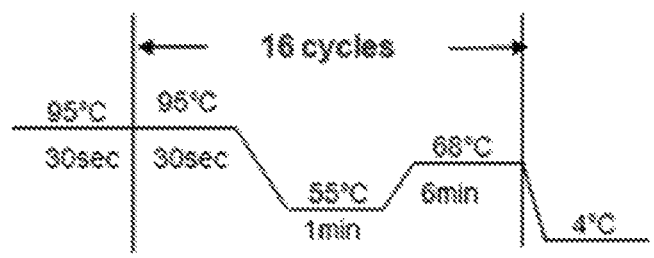
FIG. 24 depicts PCR conditions used with the mixture of the first part of Table 3.
Figure 25:
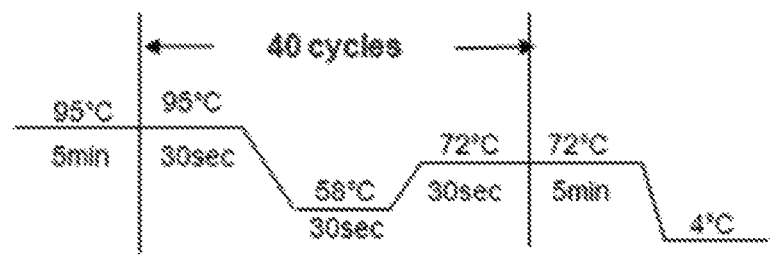
FIG. 25 depicts PCR conditions used with the mixture of the second part of Table 3.

As a result, as shown in FIG. 22, A_intact peptide reduced C8161 invasion by 10% and 45% at the concentration of 30 µg/ml and 100 µg/ml, respectively. In addition, B_intact peptide reduced invasion by 48% and 70% at the concentration of 30 µg/ml and 100 µg/ml, respectively. A_intact-Fc fusion protein also decreased C8161 invasion by 68% at the concentration of 30 µg/ml.

These results suggest that reduction of in vivo metastasis of C8161 cells by A_intact peptide or A_intact-Fc fusion protein is associated with inhibition of in vitro invasion.

Manufacturing Example 1: Preparation of Pharmaceutical Formulations

1. Preparation of Powders

| | |
|---|---|
| C12orf59 or a fragment thereof | 2 g |
| Lactose | 1 g |

Powders were prepared by mixing all the above components, which were filled in airtight packs according to the conventional method for preparing powders.

2. Preparation of Tablets

| | |
|---|---|
| C12orf59 or a fragment thereof | 100 mg |
| Corn starch | 100 mg |
| Lactose | 100 mg |
| Magnesium stearate | 2 mg |

Tablets were prepared by mixing all the above components by the conventional method for preparing tablets.

3 Preparation of Capsules

| | |
|---|---|
| C12orf59 or a fragment thereof | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

5. Preparation of Injectable Solutions

| | |
|---|---|
| C12orf59 or a fragment thereof | 10 μg/ml |
| Weak HCl BP | until pH 7.6 |
| Injectable NaCl BP | up to 1 ml |

C12orf59 protein was dissolved in proper volume of injectable NaCl BP. pH of the prepared solution was regulated as 7.6 by using weak HCl BP. The volume was adjusted by using injectable NaCl BP. The solution was well mixed and filled in 5 and type I transparent glass ampoules. The ampoules were sealed by melting the glass of opening, followed by autoclave at 120° C. for at least 15 minutes for sterilization.

6. Preparation of Pills

| | |
|---|---|
| C12orf59 or a fragment thereof | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

7. Preparation of Granules

| | |
|---|---|
| C12orf59 or a fragment thereof | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

INDUSTRIAL APPLICABILITY

As explained hereinbefore, the C12orf59 protein or a fragment thereof of the present invention effectively inhibits cancer cell invasion and survivability. Therefore, the C12orf59 protein or the polynucleotide encoding the same can be effectively used as a pharmaceutical composition for preventing and treating cancer. In addition, the C12orf59 protein of the present invention can be effectively used not only for the prevention or treatment of cancer or for screening an agent for diagnosing or treating cancer but also for the preparation of a pharmaceutical composition for preventing and treating cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating cancer in a subject indeed thereof, comprising administering to the subject an effective amount of a pharmaceutical composition comprising an isolated anti-cancer peptide, wherein the peptide consists of an amino acid sequence selected from the group consisting of SEQ ID NOS: 30 to 37 and 39.

2. The method of claim 1, wherein the cancer is selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma.

3. The method of claim 1, wherein the peptide inhibits cancer cell invasion.

4. A method for inhibiting cancer cell invasion or metastasis in a subject indeed thereof, comprising administering to the subject an effective amount of a pharmaceutical composition comprising an isolated anti-cancer peptide, wherein the peptide consists of an amino acid sequence selected from the group consisting of SEQ ID NOS: 30 to 37 and 39.

5. The method of claim 4, wherein the cancer is selected from the group consisting of esophageal cancer, stomach cancer, colorectal cancer, oral cancer, pharyngeal cancer, laryngeal cancer, lung cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, melanoma, brain cancer, thyroid cancer, leukemia, Hodgkin's disease, lymphoma and multiple myeloma.

6. The method of claim 1, wherein the peptide is in the form of a C-terminal amidated peptide, a N-terminal acetylated peptide, a biotinylated peptide, a peptide comprising a non-natural amino acid, a peptide comprising protecting group, a peptide comprising a chemically-modified amino acid, a carboxymethylated peptide, a cyclic peptide, a dimeric peptide, or a peptide conjugated to a carrier.

7. The method of claim 1, wherein the peptide is in the form of a peptide conjugated to a carrier, and the carrier is selected from the group consisting of polyethylene glycol (PEG), enzyme, immunogloblulin Fc region, albumin, and keyhole limpet hemocyanin.

8. The method of claim 4, wherein the peptide is in the form of a C-terminal amidated peptide, a N-terminal acetylated peptide, a biotinylated peptide, a peptide comprising a non-natural amino acid, a peptide comprising protecting group, a peptide comprising a chemically-modified amino acid, a carboxymethylated peptide, a cyclic peptide, a dimeric peptide, or a peptide conjugated to a carrier.

9. The method of claim 4, wherein the peptide is in the form of a peptide conjugated to a carrier, and the carrier is selected from the group consisting of polyethylene glycol (PEG), enzyme, immunogloblulin Fc region, albumin, and keyhole limpet hemocyanin.

10. The method of claim 1, wherein the peptide consists of the amino acid sequence selected from the group consisting of SEQ ID NOS: 30 and 34.

11. The method of claim 1, wherein the peptide consists of the amino acid sequence of SEQ ID NO: 31.

12. The method of claim 1, wherein the peptide consists of the amino acid sequence of SEQ ID NO: 32.

13. The method of claim 1, wherein the peptide consists of the amino acid sequence of SEQ ID NO: 33.

14. The method of claim 1, wherein the peptide consists of the amino acid sequence of SEQ ID NO: 35.

15. The method of claim 1, wherein the peptide consists of the amino acid sequence of SEQ ID NO: 36 or 39.

16. The method of claim 1, wherein the peptide consists of the amino acid sequence of SEQ ID NO: 37.

17. The method of claim 1, wherein the cancer is colorectal cancer.

18. The method of claim 4, wherein the cancer is colorectal cancer.

19. A method for reducing cancer cell invasion or metastasis in a subject indeed thereof, comprising administering to the subject an effective amount of a pharmaceutical composition comprising an isolated anti-cancer peptide, wherein the peptide consists of an amino acid sequence selected from the group consisting of SEQ ID NOS: 30 to 37 and 39.

* * * * *

SEQUENCE LISTING

```
<160> NUMBER OF SEQ ID NOS: 39

<210> SEQ ID NO 1
<211> LENGTH: 183
<212> TYPE: PRT
<213> ORGANISM: Homo sapiens

<400> SEQUENCE: 1

Met Gly Val Arg Val His Val Val Ala Ala Ser Ala Leu Leu Tyr Phe
 1               5                  10                  15

Ile Leu Leu Ser Gly Thr Arg Cys Glu Glu Asn Cys Gly Asn Pro Glu
             20                  25                  30

His Cys Leu Thr Thr Asp Trp Val His Leu Trp Tyr Ile Trp Leu Leu
         35                  40                  45

Val Val Ile Gly Ala Leu Leu Leu Leu Cys Gly Leu Thr Ser Leu Cys
     50                  55                  60
```

```
Phe Arg Cys Cys Cys Leu Ser Arg Gln Gln Asn Gly Glu Asp Gly Gly
 65                  70                  75                  80

Pro Pro Pro Cys Glu Val Thr Val Ile Ala Phe Asp His Asp Ser Thr
                 85                  90                  95

Leu Gln Ser Thr Ile Thr Ser Leu Gln Ser Val Phe Gly Pro Ala Ala
            100                 105                 110

Arg Arg Ile Leu Ala Val Ala His Ser His Ser Ser Leu Gly Gln Leu
        115                 120                 125

Pro Ser Ser Leu Asp Thr Leu Pro Gly Tyr Glu Glu Ala Leu His Met
130                 135                 140

Ser Arg Phe Thr Val Ala Met Cys Gly Gln Lys Ala Pro Asp Leu Pro
145                 150                 155                 160

Pro Val Pro Glu Glu Lys Gln Leu Pro Pro Thr Glu Lys Glu Ser Thr
                165                 170                 175

Arg Ile Val Asp Ser Trp Asn
            180

<210> SEQ ID NO 2
<211> LENGTH: 163
<212> TYPE: PRT
<213> ORGANISM: Homo sapiens

<400> SEQUENCE: 2

Met Ser Trp Arg Pro Gln Pro Cys Cys Ile Ser Ser Cys Cys Leu Thr
  1               5                  10                  15

Thr Asp Trp Val His Leu Trp Tyr Ile Trp Leu Leu Val Ile Gly
                 20                  25                  30

Ala Leu Leu Leu Leu Cys Gly Leu Thr Ser Leu Cys Phe Arg Cys Cys
             35                  40                  45

Cys Leu Ser Arg Gln Gln Asn Gly Glu Asp Gly Gly Pro Pro Cys
         50                  55                  60

Glu Val Thr Val Ile Ala Phe Asp His Asp Ser Thr Leu Gln Ser Thr
 65                  70                  75                  80

Ile Thr Ser Leu Gln Ser Val Phe Gly Pro Ala Ala Arg Arg Ile Leu
                 85                  90                  95

Ala Val Ala His Ser His Ser Ser Leu Gly Gln Leu Pro Ser Ser Leu
            100                 105                 110

Asp Thr Leu Pro Gly Tyr Glu Glu Ala Leu His Met Ser Arg Phe Thr
        115                 120                 125

Val Ala Met Cys Gly Gln Lys Ala Pro Asp Leu Pro Pro Val Pro Glu
130                 135                 140

Glu Lys Gln Leu Pro Pro Thr Glu Lys Glu Ser Thr Arg Ile Val Asp
145                 150                 155                 160

Ser Trp Asn

<210> SEQ ID NO 3
<211> LENGTH: 21
<212> TYPE: DNA
<213> ORGANISM: Artificial Sequence
<220> FEATURE:
<223> OTHER INFORMATION: C12orf59 forward primer

<400> SEQUENCE: 3
cagccctgct gtatttcatc c                                            21

<210> SEQ ID NO 4
```

```
<211> LENGTH: 19
<212> TYPE: DNA
<213> ORGANISM: Artificial Sequence
<220> FEATURE:
<223> OTHER INFORMATION: C12orf59 reverse primer

<400> SEQUENCE: 4
ggccaaacac cgactgcag                                              19

<210> SEQ ID NO 5
<211> LENGTH: 21
<212> TYPE: DNA
<213> ORGANISM: Artificial Sequence
<220> FEATURE:
<223> OTHER INFORMATION: beta-actin forward primer

<400> SEQUENCE: 5
gctcgtcgtc gacaacggct c                                           21

<210> SEQ ID NO 6
<211> LENGTH: 25
<212> TYPE: DNA
<213> ORGANISM: Artificial Sequence
<220> FEATURE:
<223> OTHER INFORMATION: beta-actin reverse primer

<400> SEQUENCE: 6
caaacatgat ctgggtcatc ttctc                                       25

<210> SEQ ID NO 7
<211> LENGTH: 19
<212> TYPE: RNA
<213> ORGANISM: Artificial Sequence
<220> FEATURE:
<223> OTHER INFORMATION: C12orf59 specific siRNA

<400> SEQUENCE: 7
ggguacaucu cugguauau                                              19

<210> SEQ ID NO 8
<211> LENGTH: 19
<212> TYPE: RNA
<213> ORGANISM: Artificial Sequence
<220> FEATURE:
<223> OTHER INFORMATION: C12orf59 specific siRNA

<400> SEQUENCE: 8
ucacaucucu gcagucggu                                              19

<210> SEQ ID NO 9
<211> LENGTH: 19
<212> TYPE: RNA
<213> ORGANISM: Artificial Sequence
<220> FEATURE:
<223> OTHER INFORMATION: C12orf59 specific siRNA

<400> SEQUENCE: 9
gaauaguuga cucuuggaa                                              19

<210> SEQ ID NO 10
<211> LENGTH: 19
<212> TYPE: RNA
<213> ORGANISM: Artificial Sequence
<220> FEATURE:
<223> OTHER INFORMATION: C12orf59 specific siRNA

<400> SEQUENCE: 10
```
gguucuuacu cuucguuca                                              19

<210> SEQ ID NO 11
<211> LENGTH: 21
<212> TYPE: DNA
<213> ORGANISM: Artificial Sequence
<220> FEATURE:
<223> OTHER INFORMATION: control siRNA

<400> SEQUENCE: 11
cuuacgcuga guacuucgat t                                           21

<210> SEQ ID NO 12
<211> LENGTH: 21
<212> TYPE: DNA
<213> ORGANISM: Artificial Sequence
<220> FEATURE:
<223> OTHER INFORMATION: control siRNA antisense

<400> SEQUENCE: 12
ucgaaguacu cagcguaagt t                                           21

<210> SEQ ID NO 13
<211> LENGTH: 35
<212> TYPE: DNA
<213> ORGANISM: Artificial Sequence
<220> FEATURE:
<223> OTHER INFORMATION: pcDNA-myc forward primer

<400> SEQUENCE: 13
ctcagaagag gatctgtaaa gcgccgtcga ccatc                            35

<210> SEQ ID NO 14
<211> LENGTH: 35
<212> TYPE: DNA
<213> ORGANISM: Artificial Sequence
<220> FEATURE:
<223> OTHER INFORMATION: pcDNA-myc reverse primer

<400> SEQUENCE: 14
gatggtcgac ggcgctttac agatcctctt ctgag                            35

<210> SEQ ID NO 15
<211> LENGTH: 35
<212> TYPE: DNA
<213> ORGANISM: Artificial Sequence
<220> FEATURE:
<223> OTHER INFORMATION: pcDNA-C12orf59-isoform1-myc forward primer

<400> SEQUENCE: 15
aacatctcga ggccgccatg ggagtccgag ttcat                            35

<210> SEQ ID NO 16
<211> LENGTH: 32
<212> TYPE: DNA
<213> ORGANISM: Artificial Sequence
<220> FEATURE:
<223> OTHER INFORMATION: pcDNA-C12orf59-isoform1-myc reverse primer

<400> SEQUENCE: 16
aattcaagct tgttccaaga gtcaactatt cg                               32

<210> SEQ ID NO 17
<211> LENGTH: 35
<212> TYPE: DNA

```
<213> ORGANISM: Artificial Sequence
<220> FEATURE:
<223> OTHER INFORMATION: pcDNA-C12orf59-isoform1del-myc forward primer

<400> SEQUENCE: 17
aacatctcga ggccgccatg ggagtccgag ttcat                         35

<210> SEQ ID NO 18
<211> LENGTH: 27
<212> TYPE: DNA
<213> ORGANISM: Artificial Sequence
<220> FEATURE:
<223> OTHER INFORMATION: pcDNA-C12orf59-isoform1del-myc reverse primer

<400> SEQUENCE: 18
aattcaagct tgcggaagca cagggac                                  27

<210> SEQ ID NO 19
<211> LENGTH: 35
<212> TYPE: DNA
<213> ORGANISM: Artificial Sequence
<220> FEATURE:
<223> OTHER INFORMATION: pcDNA-C12orf59-isoform1 forward primer

<400> SEQUENCE: 19
aacatctcga ggccgccatg ggagtccgag ttcat                         35

<210> SEQ ID NO 20
<211> LENGTH: 35
<212> TYPE: DNA
<213> ORGANISM: Artificial Sequence
<220> FEATURE:
<223> OTHER INFORMATION: pcDNA-C12orf59-isoform1 reverse primer

<400> SEQUENCE: 20
aattcaagct ttcagttcca agagtcaact attcg                         35

<210> SEQ ID NO 21
<211> LENGTH: 33
<212> TYPE: DNA
<213> ORGANISM: Artificial Sequence
<220> FEATURE:
<223> OTHER INFORMATION: pcDNA-C12orf59-isoform2-myc forward primer

<400> SEQUENCE: 21
aacatctcga ggccgccatg tcgtggcggc ctc                           33

<210> SEQ ID NO 22
<211> LENGTH: 32
<212> TYPE: DNA
<213> ORGANISM: Artificial Sequence
<220> FEATURE:
<223> OTHER INFORMATION: pcDNA-C12orf59isoform2-myc reverse primer

<400> SEQUENCE: 22
aattcaagct tgttccaaga gtcaactatt cg                            32

<210> SEQ ID NO 23
<211> LENGTH: 33
<212> TYPE: DNA
<213> ORGANISM: Artificial Sequence
<220> FEATURE:
<223> OTHER INFORMATION: pcDNA-C12orf59isoform2 forward primer

<400> SEQUENCE: 23
aacatctcga ggccgccatg tcgtggcggc ctc                           33
```

```
<210> SEQ ID NO 24
<211> LENGTH: 35
<212> TYPE: DNA
<213> ORGANISM: Artificial Sequence
<220> FEATURE:
<223> OTHER INFORMATION: pcDNA-C12orf59isoform2 reverse primer

<400> SEQUENCE: 24
aattcaagct ttcagttcca agagtcaact attcg                              35

<210> SEQ ID NO 25
<211> LENGTH: 27
<212> TYPE: DNA
<213> ORGANISM: Artificial Sequence
<220> FEATURE:
<223> OTHER INFORMATION: human integrin a5 promoter-forward primer

<400> SEQUENCE: 25
ccgctcgagg agctgaaggt tgggtcc                                       27

<210> SEQ ID NO 26
<211> LENGTH: 24
<212> TYPE: DNA
<213> ORGANISM: Artificial Sequence
<220> FEATURE:
<223> OTHER INFORMATION: human integrin a5 promoter-reverse primer

<400> SEQUENCE: 26
ccgctcgagc cgtctgttcc cggc                                          24

<210> SEQ ID NO 27
<211> LENGTH: 66
<212> TYPE: PRT
<213> ORGANISM: Homo sapiens

<400> SEQUENCE: 27

Met Gly Val Arg Val His Val Val Ala Ala Ser Ala Leu Leu Tyr Phe
 1               5                  10                  15

Ile Leu Ser Gly Thr Arg Cys Glu Glu Asn Cys Gly Asn Pro Glu
            20                  25                  30

His Cys Leu Thr Thr Asp Trp Val His Leu Trp Tyr Ile Trp Leu Leu
        35                  40                  45

Val Val Ile Gly Ala Leu Leu Leu Cys Gly Leu Thr Ser Leu Cys
    50                  55                  60

Phe Arg
 65

<210> SEQ ID NO 28
<211> LENGTH: 17
<212> TYPE: PRT
<213> ORGANISM: Artificial Sequence
<220> FEATURE:
<223> OTHER INFORMATION: A_intact

<400> SEQUENCE: 28

Glu Glu Asn Cys Gly Asn Pro Glu His Cys Leu Thr Thr Asp Trp Val
 1               5                  10                  15

His

<210> SEQ ID NO 29
<211> LENGTH: 20
<212> TYPE: PRT
```

-continued

```
<213> ORGANISM: Artificial Sequence
<220> FEATURE:
<223> OTHER INFORMATION: B_intact

<400> SEQUENCE: 29

Ser Trp Arg Pro Gln Pro Cys Cys Ile Ser Ser Cys Cys Leu Thr Thr
1               5                   10                  15

Asp Trp Val His
            20

<210> SEQ ID NO 30
<211> LENGTH: 12
<212> TYPE: PRT
<213> ORGANISM: Artificial Sequence
<220> FEATURE:
<223> OTHER INFORMATION: A_N-term

<400> SEQUENCE: 30

Asn Pro Glu His Cys Leu Thr Thr Asp Trp Val His
1               5                   10

<210> SEQ ID NO 31
<211> LENGTH: 12
<212> TYPE: PRT
<213> ORGANISM: Artificial Sequence
<220> FEATURE:
<223> OTHER INFORMATION: A_C-term1

<400> SEQUENCE: 31

Glu Glu Asn Cys Gly Asn Pro Glu His Cys Leu Thr
1               5                   10

<210> SEQ ID NO 32
<211> LENGTH: 7
<212> TYPE: PRT
<213> ORGANISM: Artificial Sequence
<220> FEATURE:
<223> OTHER INFORMATION: A_Cen

<400> SEQUENCE: 32

Asn Pro Glu His Cys Leu Thr
1               5

<210> SEQ ID NO 33
<211> LENGTH: 7
<212> TYPE: PRT
<213> ORGANISM: Artificial Sequence
<220> FEATURE:
<223> OTHER INFORMATION: A_C-term2

<400> SEQUENCE: 33

Glu Glu Asn Cys Gly Asn Pro
1               5

<210> SEQ ID NO 34
<211> LENGTH: 15
<212> TYPE: PRT
<213> ORGANISM: Artificial Sequence
<220> FEATURE:
<223> OTHER INFORMATION: B_N-term

<400> SEQUENCE: 34

Pro Cys Cys Ile Ser Ser Cys Cys Leu Thr Thr Asp Trp Val His
1               5                   10                  15

<210> SEQ ID NO 35
```

```
<211> LENGTH: 15
<212> TYPE: PRT
<213> ORGANISM: Artificial Sequence
<220> FEATURE:
<223> OTHER INFORMATION: B_C-term1

<400> SEQUENCE: 35

Ser Trp Arg Pro Gln Pro Cys Cys Ile Ser Ser Cys Cys Leu Thr
 1               5                  10                  15

<210> SEQ ID NO 36
<211> LENGTH: 10
<212> TYPE: PRT
<213> ORGANISM: Artificial Sequence
<220> FEATURE:
<223> OTHER INFORMATION: B_Cen

<400> SEQUENCE: 36

Pro Cys Cys Ile Ser Ser Cys Cys Leu Thr
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: B_C-term2

<400> SEQUENCE: 37

Ser Trp Arg Pro Gln Pro Cys Cys Ile Ser
 1               5                  10

<210> SEQ ID NO 38
<211> LENGTH: 8
<212> TYPE: PRT
<213> ORGANISM: Artificial Sequence
<220> FEATURE:
<223> OTHER INFORMATION: A/B common

<400> SEQUENCE: 38

Cys Leu Thr Thr Asp Trp Val His
 1               5

<210> SEQ ID NO 39
<211> LENGTH: 6
<212> TYPE: PRT
<213> ORGANISM: Artificial Sequence
<220> FEATURE:
<223> OTHER INFORMATION: B_Cen2

<400> SEQUENCE: 39

Pro Cys Cys Ile Ser Ser
 1               5
```